United States Patent [19]
Machida

[11] Patent Number: 4,537,203
[45] Date of Patent: Aug. 27, 1985

[54] ABNORMAL CELL DETECTING DEVICE
[75] Inventor: Kaoru Machida, Otawara, Japan
[73] Assignee: Tokyo Shibaura Denki Kabushiki Kaisha, Kawasaki, Japan
[21] Appl. No.: 623,549
[22] Filed: Jun. 25, 1984

Related U.S. Application Data
[63] Continuation of Ser. No. 311,911, Oct. 16, 1981, abandoned.

[30] Foreign Application Priority Data
Oct. 21, 1980 [JP] Japan ................. 55-147408
[51] Int. Cl.³ ............................... A61B 5/05
[52] U.S. Cl. ..................................... 128/734
[58] Field of Search .............................. 128/734

[56] References Cited
U.S. PATENT DOCUMENTS
3,316,896 5/1967 Thomasset ................. 128/734
3,320,946 5/1967 Dethloff et al. .............. 128/734
4,263,920 4/1981 Tasto et al. ................. 128/734

OTHER PUBLICATIONS
Singh et al., Med. & Biol. Eng. & Comput., vol. 17, No. 1, (Jan. 1979), pp. 45–60.
Kemelman, "Abnormal Electric Properties Betray Breast Tumors to Scanner," Electronics, vol. 53, No. 1, Jan. 3, 1980, pp. 68–70.

Primary Examiner—Kyle L. Howell
Assistant Examiner—John C. Hanley
Attorney, Agent, or Firm—Finnegan, Henderson, Farabow, Garrett & Dunner

[57] ABSTRACT
This invention discloses an abnormal cell detecting device having at least a pair of electrodes to be attached to a portion of a body. At least one electrode of the pair of electrodes is constituted by a plurality of independent electrodes cells. One voltage at a frequency is applied between the pair of electrodes, and another voltage of a different frequency is applied between them. As a result, electrostatic capacitances corresponding to the two frequencies are measured between the electrodes as voltages by a capacitance measuring unit. The ratio of the voltages is calculated by a division unit, and the resultant ratio is digitally sent out through an A/D converter to a memory unit. Digital signals corresponding to a plurality of electrode cells are stored as image data in the memory unit. A display unit displays the position and size of abnormal cells, based on the image data of the memory unit.

6 Claims, 55 Drawing Figures

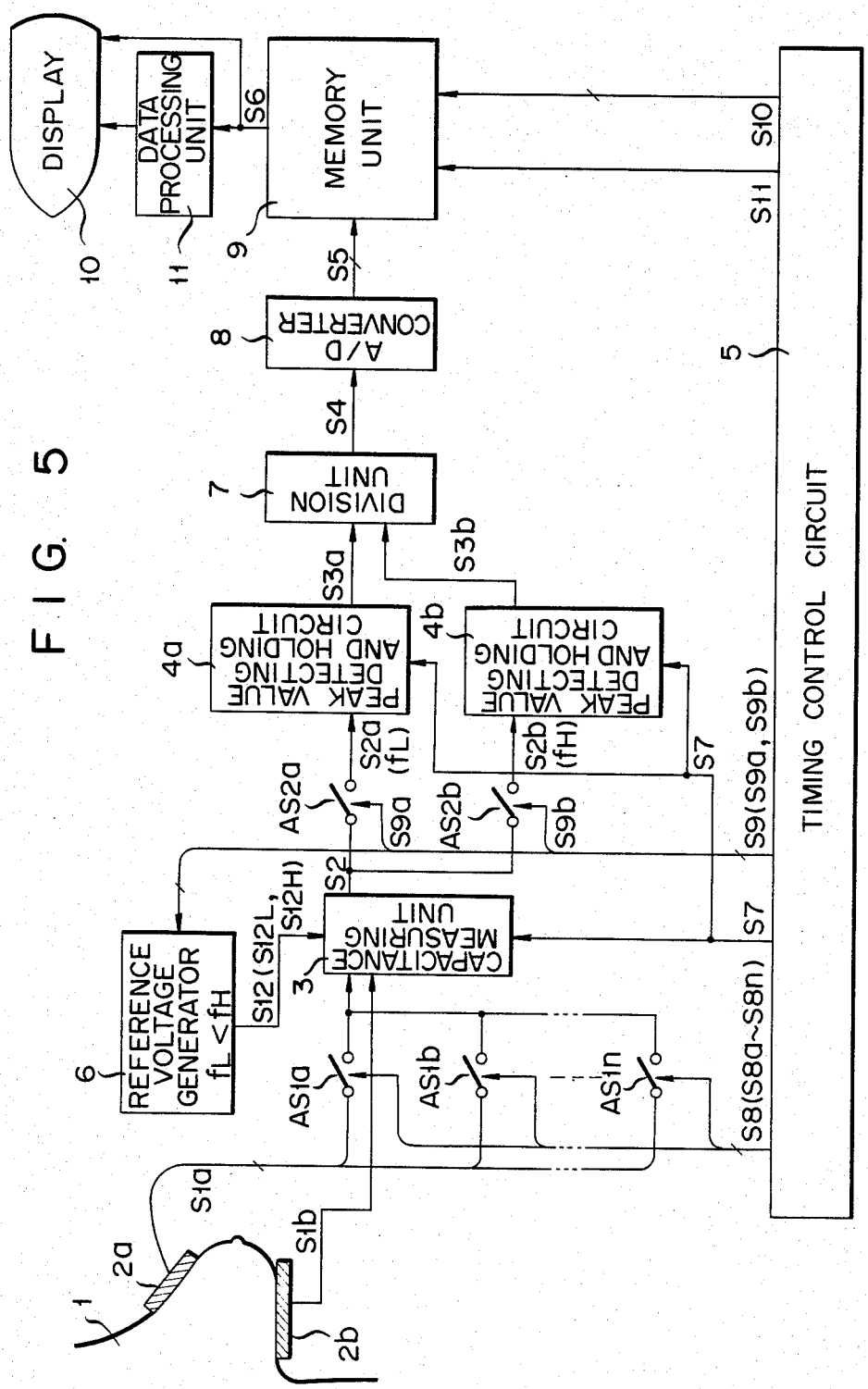
F I G. 5

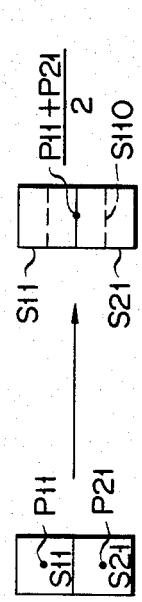
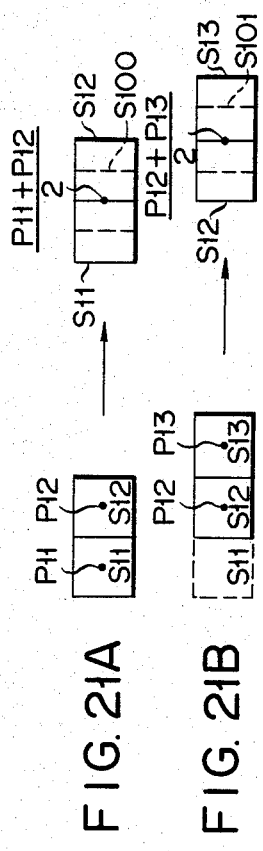
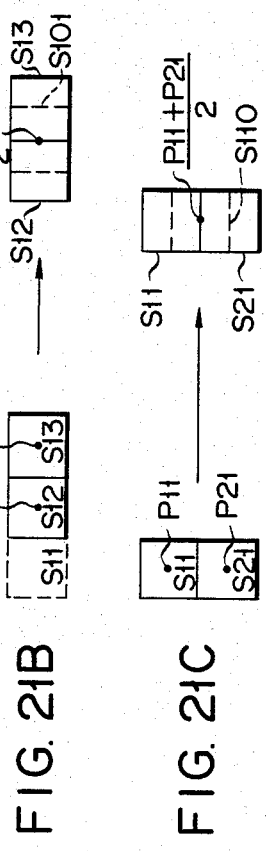
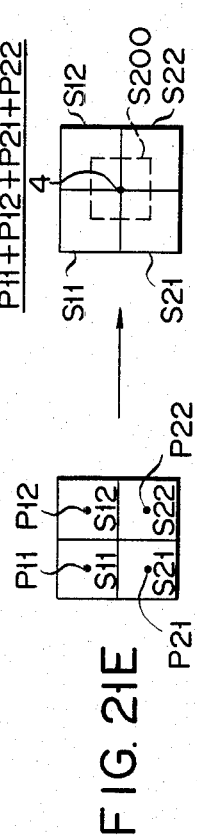
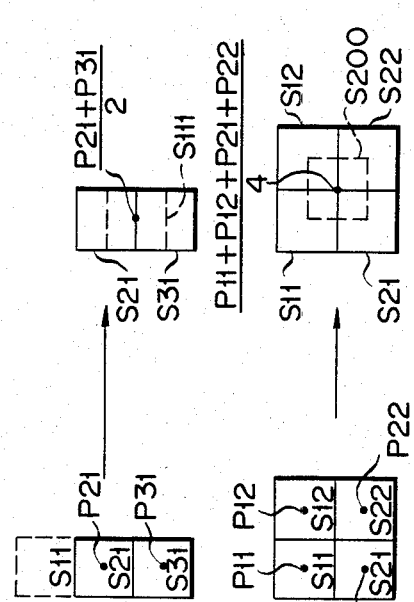
FIG. 21A
FIG. 21B
FIG. 21C
FIG. 21D
FIG. 21E
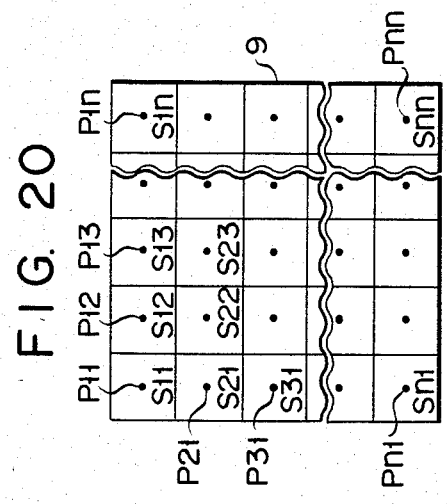
FIG. 20
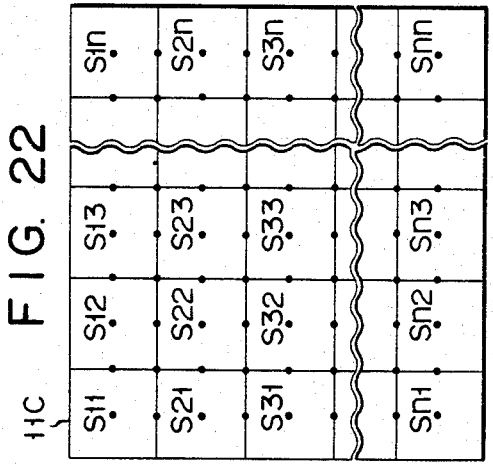
FIG. 22

ABNORMAL CELL DETECTING DEVICE

This application is a continuation of application Ser. No. 311,911, filed Oct. 16, 1981 now abandoned.

BACKGROUND OF THE INVENTION

The present invention relates to an abnormal cell detecting device in which cancer cells may be detected in a nonoperative and non-invasive manner, for example, in an examination for breast cancer.

Conventionally, palpitation and diagnostic devices utilizing X-ray mammography, ultrasonic scanning and thermography have been proposed to diagnose abnormal cells in the human body, for example, breast cancer cells. However, since X-ray mammography may cause radiation-related illnesses such as birth defects or cancer, even if X-ray mammography is better than ultrasonic scanning and thermography in resolution, the use of X-ray mammography tends to be limited in countries such as the United States of America. Even though use of the ultrasonic scanner has become wide spread, its resolution is not good enough for early detection of breast cancer. The practical application of thermography has not yet been established.

Recently, a mammo-scanner as shown in FIG. 1 has been introduced. With this scanner, electrodes 2a and 2b are respectively attached to the skin of a portion of a body 1 including a breast, and the corresponding portion of the back. Each electrode is constituted as an independent assembly of one electrode cell. The value of the electrostatic capacity from one electrode cell to the opposite electrode cell is measured in response to signals S1a and S1b which are respectively supplied from one electrode cell and the opposite cell. The presence or absence of a cancer cell is thus determined by a large or small measured value. However, since the electrodes 2a and 2b of the mammo-scanner of this type are attached respectively to the breast and to the corresponding portion on the back, the results are influenced by the organs interposed between the electrodes (that is, the cells) and their conditions, resulting in inclusion of many error components into the measured value. Further, since the shape of the breast varies, lengths lhd 1 and l₂ from one electrode to the other electrode vary so that the number of cells included in the range between the lengths also varies. Therefore, even if abnormal cells are absent in this range, the scanner may erroneously indicate that abnormal cells are present. After examination, a correction in accordance with body shape is required in order to prevent the trouble described above. Therefore, the device as a whole becomes large and complicated.

SUMMARY OF THE INVENTION

The object of the present invention is, therefore, to provide an abnormal cell detecting device with improved reliability in which abnormal cells of the human body are correctly and safely detected, while the device is not made large.

This object has been attained by an abnormal cell detecting device which comprises: at least a pair of electrodes to be attached to the skin of a living body portion to be measured; voltage generating means for supplying first and second voltages having different frequencies between said electrodes; detecting means for detecting first and second impedance values, independently, obtained from said skin portions to be measured when the first and second voltages are supplied across said electrodes; dividing means for calculating the ratio of the first and second impedance values obtained by said detecting means; memory means having at least one memory for storing the results calculated by said dividing means; data processing means for outputting image data for obtaining various effective images, based on the memory contents of said memory; and display means for displaying the output contents of said data processing means or the memory contents of said memory means.

In this way, according to the present invention, two voltages having different frequencies are applied to the skin portions to be measured and two impedances for the skin portions to be measured are obtained. The ratio of these impedances is calculated to display the position of abnormal cells. Therefore, a relatively large current need not be supplied to the skin portions being measured as opposed to conventional devices.

According to the present invention, therefore, the device has an optimal diagnostic function in detecting abnormal cells, and is improved in safety considerations in comparison with the conventional device. Further, since the structure of the device as a whole is simple, low cost and compact configuration are achieved. As compared with the mammo-scanner for detecting breast cancer, the device according to the present invention requires only small skin portions to be measured and eliminates erratic detection when the distance between the opposing electrodes varies slightly, thus increasing the diagnostic precision and improving safety since only a small current flows through the human body. For example, in the mammo-scanner, a current of about 100 μA flows between the breast and the corresponding portion on the back so that the patient's heart may be directly shocked. However, in the device according to the present invention, the electrodes are disposed at the upper and lower portions of the breast which are narrowly spaced apart and the current flow between the portions is extremely small, so that the heart is not directly shocked and safety is thus assured with excellent operability. Therefore, the device is suitable for use for group examinations.

BRIEF DESCRIPTION OF THE DRAWINGS

By way of example and to make the description clearer, reference is made to the accompanying drawings in which:

FIG. 5 is a schematic block diagram of a first embodiment of an abnormal cell detecting device according to the present invention;

FIGS. 20, 21A to 21E and 22 are views for explaining the operation of the data processing unit shown in FIG. 19.

DETAILED DESCRIPTION OF THE PREFERRED EMBODIMENTS

Figure 1:
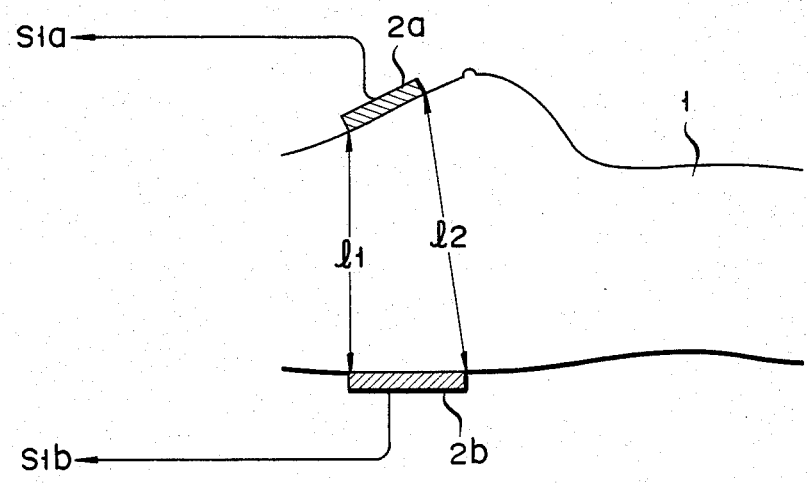
FIG. 1 shows the principle of operation for a conventional mammo-scanner.
Figure 2:
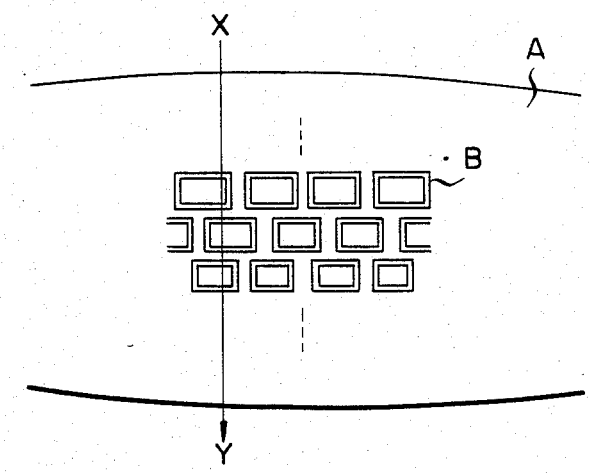
FIG. 2 is a view for illustrating a tissue.
Figure 3:
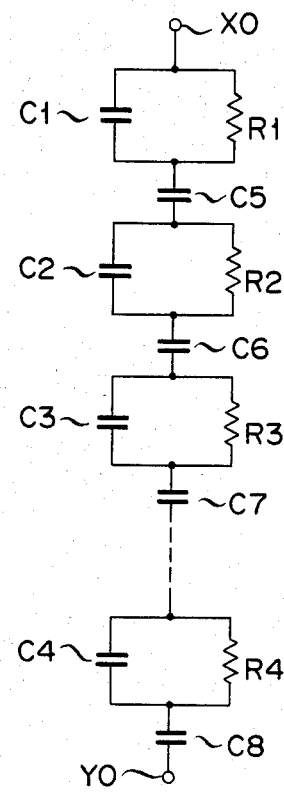
FIG. 3 is a circuit diagram which is electrically equivalent to the tissue illustrated in FIG. 2.
Figure 4:
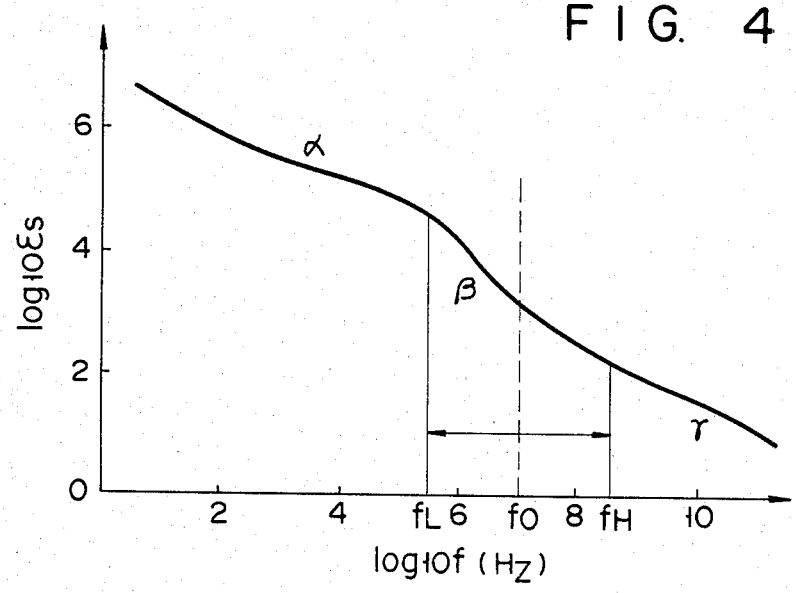
FIG. 4 shows the principle of operation according to the present invention.

FIGS. 2 to 4 are views for explaining the basic principles of the present invention. FIG. 2 is a view illustrating a model including an organism A and cells B thereof, while FIG. 3 is a circuit diagram which is electrically equivalent to the view of FIG. 2 along the line of the X-Y direction. However, the circuit diagram of FIG. 3 eliminates the skin and cell nuclei of the organism A shown in FIG. 2. This is because the skin and cell nuclei of the organism A have negligible effects on electrical characteristics. Capacitors C1 to C4 designate the electrostatic capacitance of intracellular and extracellular fluids. Resistors R1 to R4 designate the resistance of the intracellular and extracellular fluids, and capacitors C5 to C8 designate the electrostatic capacitance of plasma membranes. The electrostatic capacitance and resistance may vary in accordance with different tissues. However, a great number of cells are included in the living body portions to be measured and they align randomly, so that each tissue may be regarded as a uniform tissue from the macroscopic point of view. Therefore, the electrostatic capacitance of the cells is defined as constant and the resistance of the cells is also defined as constant. The tissues of the breast may be substantially regarded as uniform tissues, thus the above assumption is justified. The above arrangement may be expressed by relations (1) to (3).

$$C1 = C2 = C3 = C4 = Cl \quad (1)$$

$$R1 = R2 = R3 = R4 = Rl \quad (2)$$

$$C5 = C6 = C7 = C8 = Cm \quad (3)$$

FIG. 4 is a graph showing the frequency characteristic of specific inductive capacitance $\epsilon s$ of the organism tissue. When organisms vary, the details of the characteristic curves may vary. However, the characteristic curves as a whole have a similar tendency in curve shape. For example, the specific inductive capacitance $\epsilon s$ decreases near specific frequencies, that is, dispersion phenomena occurs in the three frequency ranges ($\alpha$, $\beta$ and $\gamma$). This $\beta$ dispersion is called structural dispersion and is caused by the electric constants differing in respective portions of the tissue. In the frequency range lower than frequency f0 in which the $\beta$ dispersion occurs, an externally applied voltage is mostly applied to the plasma membranes. In the frequency range higher than the frequency f0, the externally applied voltage is applied to the plasma membranes and between the extracellular and intracellular fluids. In this case, the capacitances of the intracellular and the extracellular fluids are combined with that of the plasma membranes in series as shown in FIG. 3, and the former has a value smaller than the latter, so that electrostatic capacitance to be externally measured greatly decreases when the frequency increases from the frequency f0.

With the above assumption, the equivalent circuit in FIG. 3 is taken into consideration again. A frequency lower than the frequency f0 is defined as fL, a frequency higher than the frequency f0 is defined as fH, and the number of cells between the contacts X0 and Y0 of the electrodes in the current flow path is defined as n.

The impedance (that is, the electrostatic capacitance CL) between X0 and Y0 at the frequency fL is given by relation (4) from relations (1) to (3) described above:

$$CL = Cm/n \quad (4)$$

The electrostatic capacitance CH between X0 and Y0 at the frequency fH is also given by relation (5) below:

$$CH = [(Cl \times Cm)/(Cl + Cm)]/n \quad (5)$$

The ratio of the capacitance at the frequency fL to that at the frequency fH is given independently of the number of cells n in the following relation (6).

$$CL/CH = 1 + (Cm/Cl) \quad (6)$$

For example, assume that the number of cells decreases from n to m (n>m) due to the presence of cancer cells within the range of the body portion to be measured. The number of plasma membranes decreases in accordance with the decreased number of cells. However, the electostatic capacitance (hence, the resistance) of the intracellular and extracellular fluids may be considered to be substantially the same as in the case in which n cells are present in the range of the body portion to be measured since the length between the electrodes is kept constant. Therefore, the electrostatic capacitance C'L at the frequency fL is given by the following relation (7):

$$C'L = Cm/m \quad (7)$$

In the same manner, the electrostatic capacitance C'H at the frequency fH is given by the following relation (8):

$$C'H = (Cl \cdot Cm)/(mCl + nCm) \quad (8)$$

The ratio of the capacitance at the frequency fL to that at the frequency fH is given by relation (9) below:

$$C'L/C'H = 1 + (n/m) \cdot (Cm/Cl) \quad (9)$$

Since the condition n>m is given, the following relation (10) is established taken with relations (6) and (9):

$$(C_L/C_H) < (C'_L/C'_H) \qquad (10)$$

Based on the above results, the electrostatic capacitances at the frequencies fL and fH between the electrode cells in the current flow path and the ratio thereof are calculated. The calculated result is then converted to signals by which the measured body portion is monitored as light and shaded parts, thus detecting the presence or absence of cancer cells and their location.

The principle of the present invention will now be described by way of its example.

FIG. 5 is a schematic block diagram illustrating an arrangement of a first embodiment. Electrodes 2a and 2b are attached to the upper and lower portions of a breast of a body 1 under breast cancer examination. The electrode 2a has electrode cells (not shown) therein. A signal S1a from each electrode cell constituting the electrode 2a is input to one end of an analog switch AS1a, AS1b, ..., or AS1n in accordance with each current flow path. The signal S1a is thus supplied to a capacitance measuring unit 3 through the other end of the analog switch AS1a, AS1b, ..., or AS1n, together with a signal S1b from the other electrode 2b. An output signal S12 is supplied to the capacitance measuring unit 3 from a reference voltage generator 6 which generates two voltages at two different frequencies fL and fH (the amplitude of which is the same). The capacitance measuring unit 3 sequentially and selectively supplies a voltage signal S2 corresponding to the electrostatic capacitance at the frequency fL or fH in the current path between the electrode cells. The voltage signal S2 from the capacitance measuring unit 3 is transferred to peak value detecting and holding circuits 4a and 4b through two analog switches AS2a and AS2b, respectively. Output signals S3a and S3b are supplied to a division unit 7 from the peak value detecting and holding circuits 4a and 4b. A signal S4 which indicates the ratio of the signal S3a to the signal S3b is output from the division unit 7. The signal S4 is input to an A/D converter (ADC) 8 and an output digital signal S5 is sequentially stored in a memory unit 9. A display 10 receives an output signal S6 from the memory unit 9, based on data stored in the memory unit 9. The display 10 performs display after the output signal S6 is properly processed. A data processing unit 11 operates to generate display signals representing various display modes based on the output signal S6 from the memory unit 9, and supplies the processed display signal to the display 10. A timing control circuit 5 controls the units described above. The timing control circuit 5 supplies a reset signal S7 for resetting the capacitance measuring unit 3 and the peak value detecting and holding circuits 4a and 4b, and an analog switch gate signal S8 sequentially turning on or off the analog switches As1a to As1n, a gate signal S9 for selectively switching the analog switches AS2a and AS2b and the reference voltage generator 6 in correspondence with the frequencies fL and fH, an address selection signal S10 for selecting an address of the memory unit 9, and a memory latch signal S11.

Figure 6:
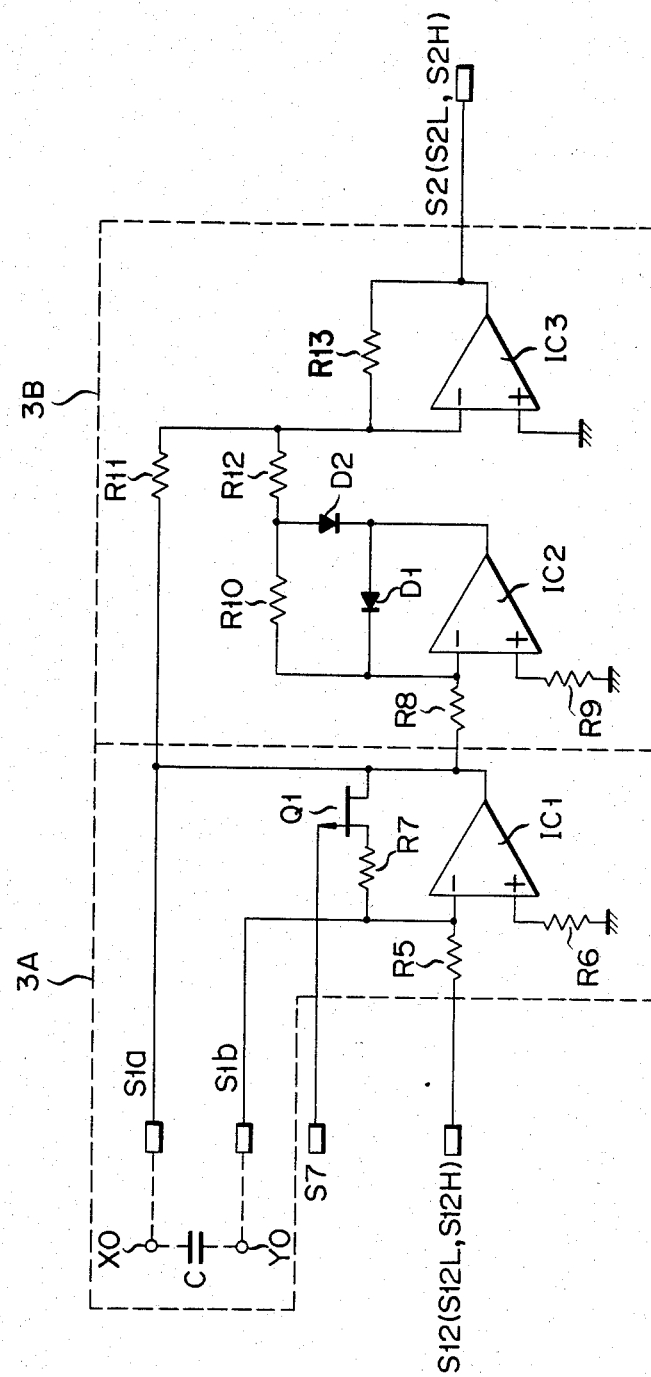
FIG. 6 is a circuit diagram of a capacitance measuring unit shown in FIG. 5.

The capacitance measuring unit 3 will be described in detail with reference to the circuit diagram shown in FIG. 6. The capacitance measuring unit 3 has an operational amplifier IC1 having resistors R5 to R7; an operational amplifier IC2 having resistors R8 to R10 and diodes D1 and D2, one input of the operation amplifier IC2 being connected to the output of the operational amplifier IC1, and an operational amplifier IC3 having resistors R11 to R13; one input of the operational amplifier IC3 being connected to the output of the operational amplifier IC2. An integration circuit 3A of the capacitance measuring unit 3 is provided with the electrodes 2a and 2b between which an organ electrostatic capacitance C is connected in the current path. That is, the organ electrostatic capacitance C is connected between the input and output ends of the operational amplifier IC1. The integration circuit 3A also includes a switching transistor Q1 driven by the reset signal S7 in the feedback path. An absolute value circuit 3B of the capacitance measuring unit 3 therefore is constituted by the operational amplifiers IC2 and IC3.

Figure 7:
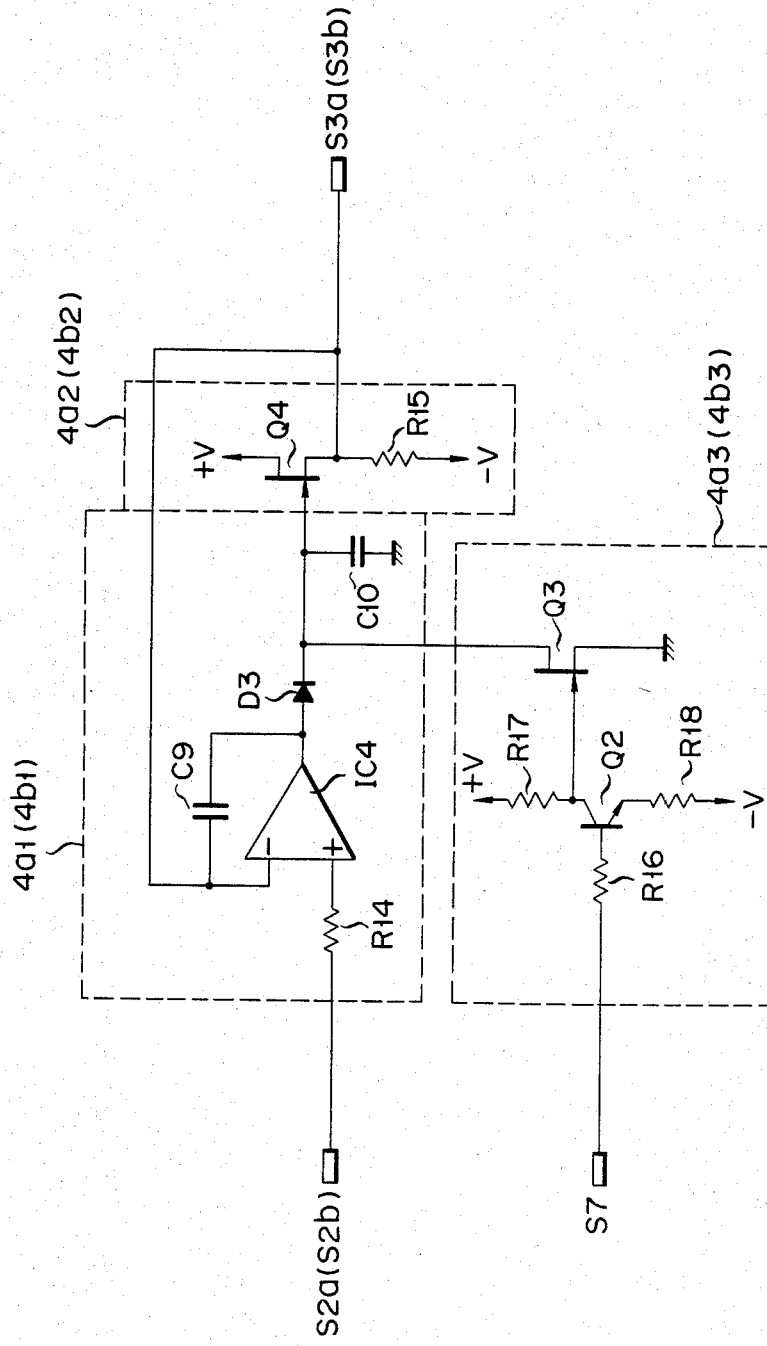
FIG. 7 is a circuit diagram of a peak value detecting and holding circuit shown in FIG. 5.

The peak value detecting and holding circuit 4a (or 4b) will be described in detail with reference to FIG. 7. The peak value detecting and holding circuit comprises a detecting and holding circuit 4a1 having a diode D3, a capacitor C10 and an operational amplifier IC4 having an input resistor R14 and a feedback capacitor C9; a source follower circuit 4a2 which is connected to the output end of the detecting and holding circuit 4a1 and which has a series circuit of an FET transistor Q4 and a resistor R15 between power sources +V and −V; and a resetting circuit 4a3 having a transistor Q2 to the base of which is applied the reset signal S7 through a resistor R16, resistors R17 and R18 being connected respectively to the collector and emitter of the transistor Q2 between the power source +V and −V, and the FET transistor Q3 being driven by the output on the collector side of the transistor Q2 and connected between the cathode of the diode D3 and ground.

Figure 8:
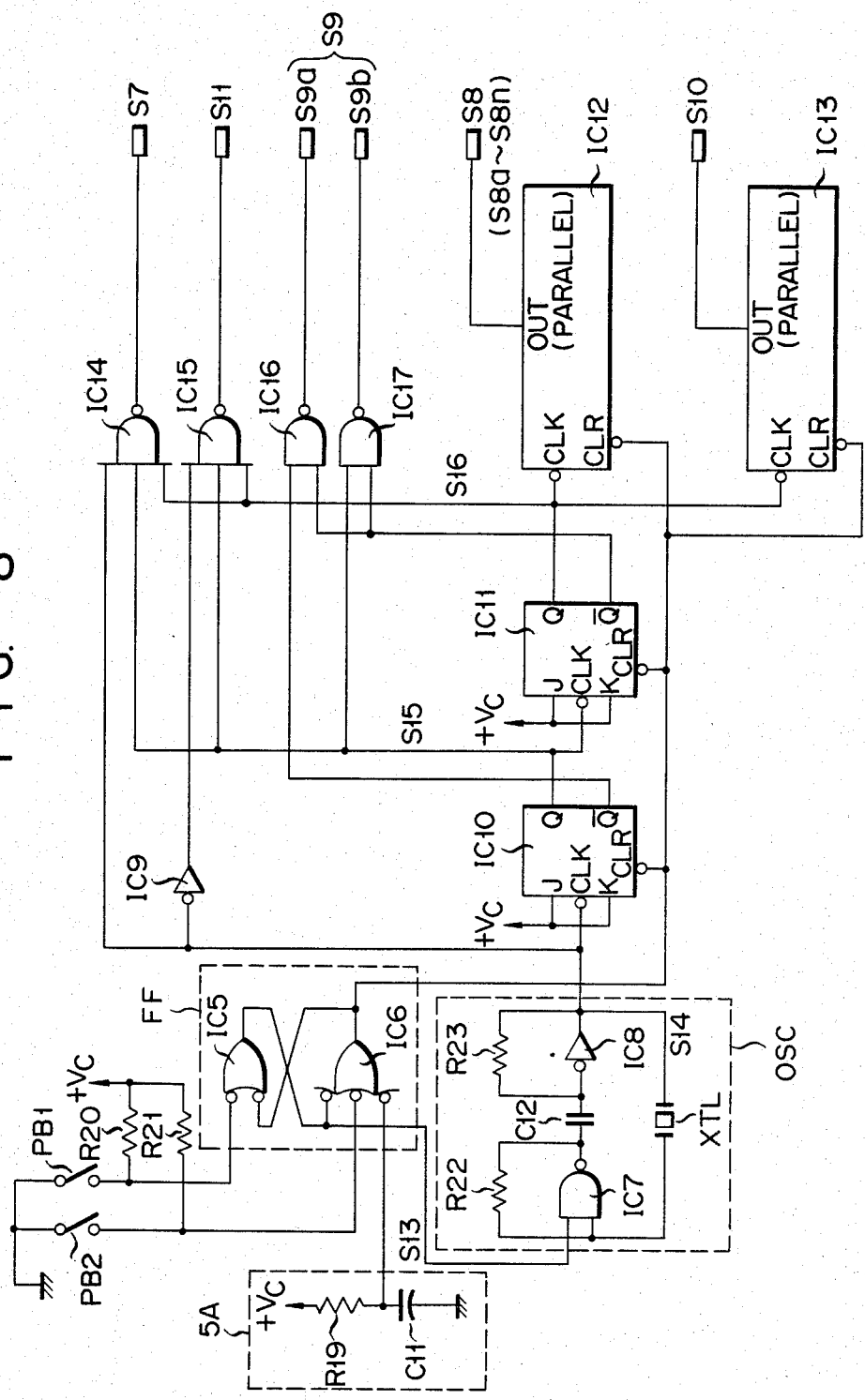
FIG. 8 is a circuit diagram of a timing control circuit shown in FIG. 5.

The timing control circuit 5 will be described in detail with reference to FIG. 8. The timing control circuit 5 comprises a power resetting circuit 5A having a resistor R19 and a capacitor C11; a flip-flop FF having gates IC5 and IC6 reset by the output from the power resetting circuit 5A and set or reset by pushbutton switches PB1 and PB2; an oscillator OSC having resistors R22 and R23, a capacitor C12, a quartz oscillator XTL, and gates IC7 and IC8 controlled by one output signal S13 from the flip-flop FF; a first JK flip-flop IC10 to a clock terminal of which is supplied the output of the oscillator OSC; a second JK flip-flop IC11 to a clock terminal of which is supplied the output of the first JK flip-flop IC10; a shift resistor IC12 and a counter IC13, the clock terminals of which receive the output from the flip-flop IC11; and four NAND gates IC14 to IC17. The JK flip-flops IC10 and IC11, the shift register IC12 and the counter IC13 of the timing control circuit 5 are all cleared by the other output of the flip-flop FF. The reset signal S7 is supplied from the NAND gate IC14 of the first stage in accordance with the status between the output from the oscillator OSC and the output from the first and second JK flip-flops IC10 and IC11. A memory latch signal S11 is supplied from the NAND gate IC15 of the next stage in accordance with the status between the inverted signal (signal inverted by an inverter IC9) from the oscillator OSC and the output from the first and second JK flip-flops IC10 and IC11. Analog switch gate signals S9a and S9b (S9) are supplied from the NAND gates IC16 and IC17 of the third and fourth stages to switch the analog switches AS2a and AS2b, respectively, in accordance with the status between the output from the first and second flip-flops IC10 and IC11. The analog switch gate signals S8 (S8a, S8b, ...

, S8n) are respectively output from n output terminals of the shift resister IC12 in order to switch the analog switches AS1a to AS1n. A binary coded address selection signal S10 is output from the counter IC13. One pushbutton switch PB1 is turned on to close the respective circuits, while the other pushbutton switch PB2 is used for opening the circuits. When the pushbutton switch PB2 is turned on, all the output signals from the timing control circuit 5 become inactive.

Figure 9:
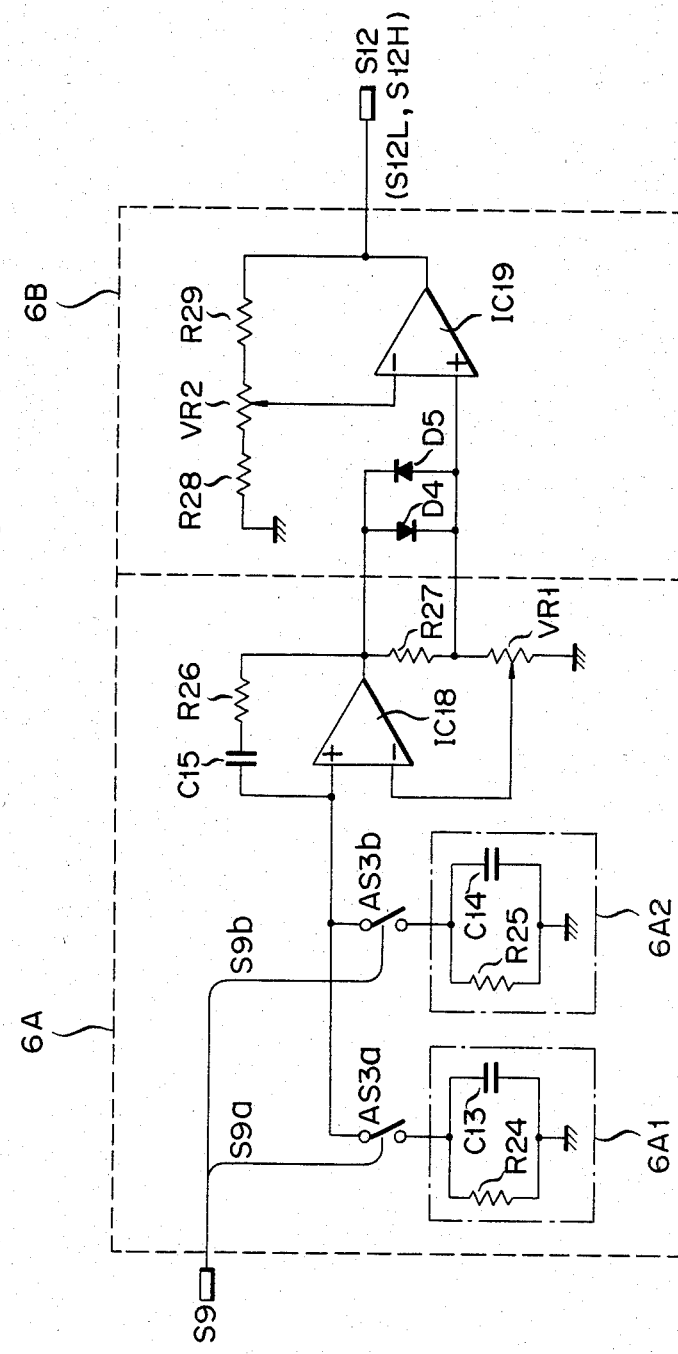
FIG. 9 is a circuit diagram of a reference voltage generator shown in FIG. 5.

The reference voltage generator 6 will be described in detail with reference to FIG. 9. The reference voltage generator 6 comprises a Wien bridge oscillator 6A having a first oscillation circuit 6A1 (constituted by a resistor R24 and a capacitor C13) connected to analog switches AS3a and AS3b which are respectively controlled by the analog switch gate signals S9a and S9b for selectively switching the analog switch AS2a for selecting the low frequency fL and the analog switch AS2b for selecting the high frequency fH, a second oscillation circuit 6A2 (constituted by a resistor R25 and a capacitor C14), and an operational amplifier IC18 having a capacitor C15, a resistor R26 and a variable resistance VR1; and a voltage follower 6B comprising an operational amplifier IC19 which receives an output from the Wien bridge oscillator 6A through diodes D4 and D5 and which has resistors R28 and R29 and a variable resistor VR2. The reference voltage generator 6 generates two kinds of reference voltages corresponding to the frequencies fL and fH as output signals S12 (S12L and S12H).

Figure 10:
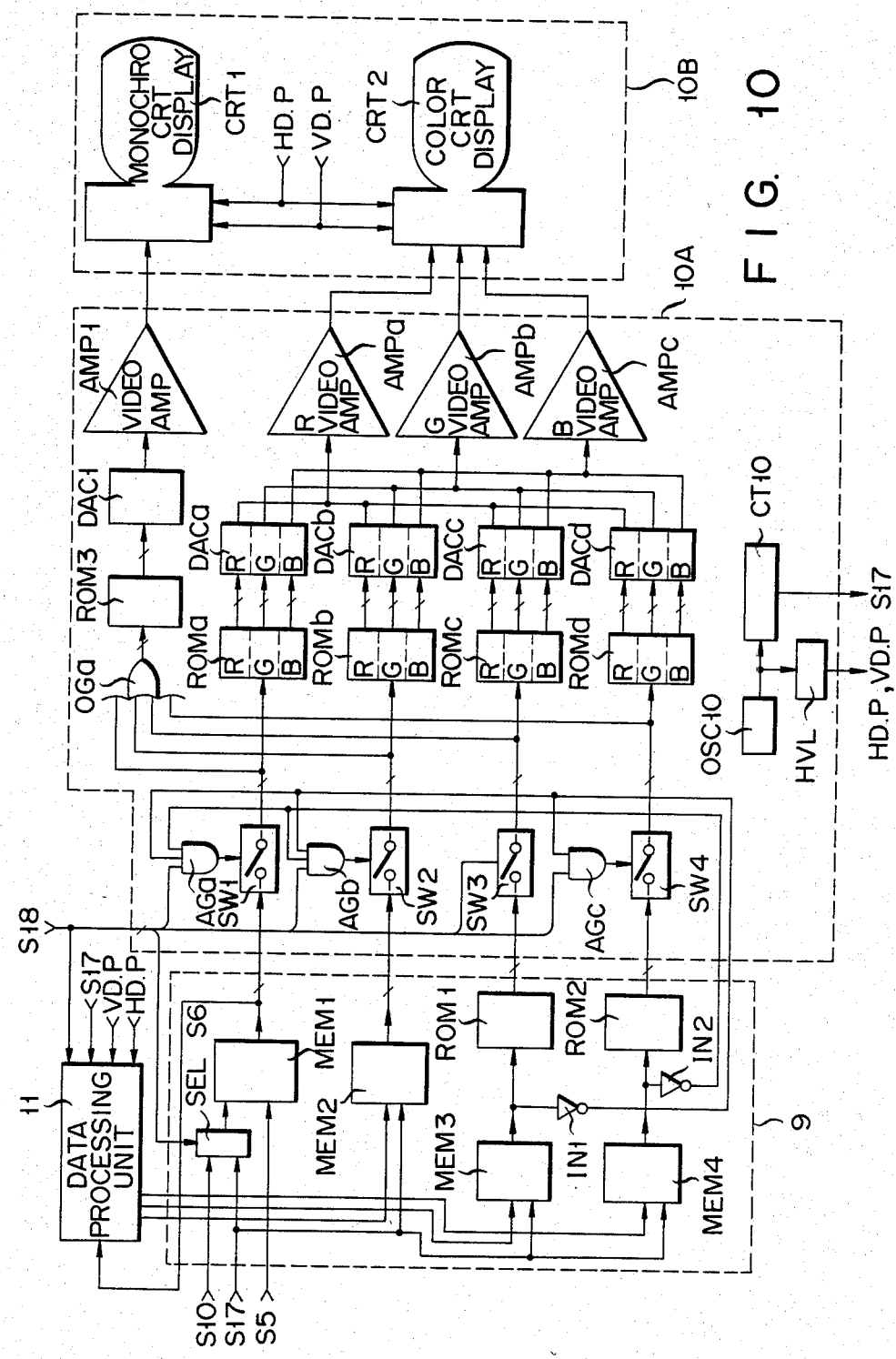
FIG. 10 is a schematic block diagram illustrating an arrangement of a memory unit and a display shown in FIG. 5.

The interrelations among the memory unit 9, the display 10 and the data processing unit 11 are described with reference to FIGS. 10 and 11.

The memory unit 9 comprises a data selector SEL for selecting a display address signal S17 which is the output signal of a display counter CT10 within the display 10 to be described later, and the address selection signal S10, based on a control signal S18 produced by an operation at a control panel (not shown); a first memory MEM1 which receives the output from the data selector SEL as address information and the output signal from the ADC 8 as data information; a second memory MEM2 for storing a value (for example, after gray scale adjustment, data corresponding to the gradation of a display, that is, a CRT) which is normalized corresponding to the electrode 2a and which is calculated by the data processing unit 11, based on the memory contents of the memory MEM1; a third memory MEM3 for storing a flag which specifies address data MSD calculated by the date processing unit 11 based on the data within the memory MEM1; a fourth memory MEM4 for storing data which designates an area of abnormal cells and binary coded data which designates the presence or absence of the abnormal cells, as judged by the data processing unit 11 based on the memory contents of the memory MEM1; and density conversion tables ROM1 and ROM2 which convert memory data (binary coded data) of the third and fourth memories MEM3 and MEM4 to binary coded data of n bits (for example, 16 bits) corresponding to a specific color or density. The first and second memories MEM1 and MEM2 have a page memory constituted by a plurality of memory media and input data converted to binary coded signals which determine the density. For example, the second memory MEM2 has an 8-page memory and creates density discriminating data of 256 gradations based on the output of the data processing unit 11 which calculates the memory contents of the first memory MEM1, thus storing binary coded density discriminating signals.

The display 10 comprises a display control section 10A and a display section 10B having a monochrome CRT display CRT1 and a color CRT display CRT2. The display control section 10A has digital switches SW1 to SW4 connected to the output ends of the first and second memories MEM1 and MEM2 and the conversion tables ROM1 and ROM2; AND gates AGa and AGb which receive the control signal S18 and the inverted signal outputs (inverted by inverters IN1 and IN2) of the third and fourth memories MEM3 and MEM4 and which control the first and second digital switches SW1 and SW2, respectively; an AND gate AGc which receives the control signal S18 and the inverted signal output from the third memory MEM3 and which controls the fourth digital switch SW4; an OR gate OGa to which is input four signal outputs through the digital switches SW1 to SW4; a density conversion table ROM3 which converts data obtained from the OR gate OGa to a density designating data and which supplies proper data suitable for CRT displays; a converter DAC1 for converting digital data from the table ROM3 to analog data; a video amplifier AMP1 which amplifies the output of the converter DAC1 and which supplies data to the monochrome CRT display CRT1; color conversion tables ROMa to ROMd which have three primary color elements of red (R), green (G) and blue (B) and which convert data obtained through the digital switches SW1 to SW4 to a suitable color signal; converters DACa to DACd for converting an output digital signal of each color signal from color conversion tables ROMa to ROMd to an analog signal; video amplifiers AMPa to AMPc to which are input the same color signal from the converters DACa to DACd and which amplify the color signal and supply the video signal to the color CRT display CRT2; an oscillator OSC10 for generating a basic clock signal for display; a counter CT10 to which is input the output pulse train from the oscillator OSC10 and which generates the display address signal S17; and a hold signal generating circuit HVL for generating a horizontal hold signal HDP and a vertical hold signal VDP which drive the monochrome CRT display CRT1 and the color CRT display CRT2 in the display section, to be described later from the output pulse from the oscillator OSC10. The upper two color conversion tables ROMa and ROMb among the color conversion tables ROMa to ROMd are preset not to select a "color" determined by the color conversion tables ROMc and ROMd which receive, respectively, the outputs from the conversion table ROM1 for displaying the maximum value and the conversion table ROM2 for displaying the area of abnormal cells.

Figure 11:
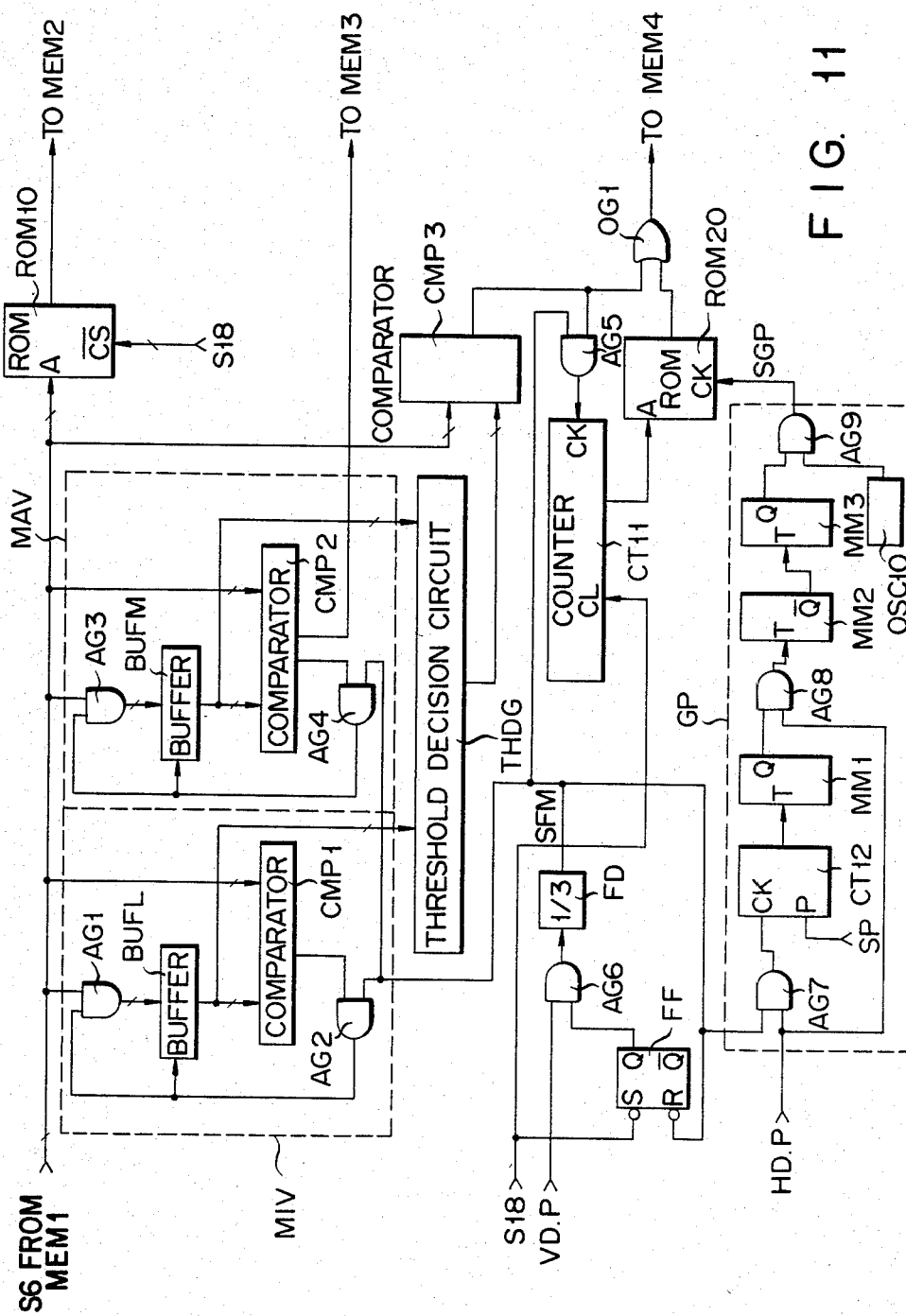
FIG. 11 is a circuit diagram of a data processing unit shown in FIG. 5.

The data processing unit 11 has an arrangement as shown in FIG. 11. The data processing unit 11 comprises a conversion table ROM10 which receives the output signal S6 from the memory MEM1 within the memory unit 9, selects a chip in response to the control signal S18, and converts the output signal S6 to normalized value data; a minimum value determining circuit MIV having AND gates AG1 and AG2, a buffer BUFL and a comparator CMP1, to which is input the signal S6 and which determines a minimum value of the signal S6; a maximum value determining circuit MAV having AND gates AG3 and AG4, a buffer BUFM and a comparator CMP2, which receives the signal S6 and which determines the maximum value of the signal S6; a threshold decision circuit THDG which receives the output signals from the buffers BUFL and BUFM which respectively store the minimum and maximum values, and which determines the threshold value in order to determine the presence or absence of abnormal cells; a comparator CMP3 which compares the output threshold value data of the threshold decision circuit and the data signal S6, and which outputs the binary signal which designates the absence or presence of abnormal cells; an RS flip-flop FF for receiving the panel control signal S18 at the set input end; an AND gate AG6 for receiving the vertical hold signal VDP and a Q output from the flip-flop FF; a frequency divider FD which divides the output from the AND gate AG6 by three, outputs a timing signal SFM corresponding to one frame, controls the AND gates AG2 and AG4 by the divided output, and resets the flip-flop FF at the trailing edge of the timing signal SFM; an AND gate AG5 for receiving the output timing signal SFM from the frequency divider FD and the output from the comparator CMP3; a counter CT11 which receives the output from the AND gate AG5 for counting and which is cleared by the panel control signal S18; a display timing signal generator GP which receives the output timing signal SFM of the frequency divider FD and the horizontal hold signal HDP and which outputs a clock pulse SGP for reading out characters from a character generator ROM20 to be described later; and the character generator ROM20 for supplying output pattern data for displaying values corresponding to the count value of the counter CT11, at the timing of the clock pulse SGP from the display timing signal generator GP as the readout signal. The character generator ROM20 stores a plurality of pattern data corresponding to, for example, a two-digit value, selects the area in which the value pattern corresponds to the count value from the counter CT11, and sequentially outputs the value pattern data. The display timing signal generator GP comprises an AND gate AG7 for receiving the output timing signal SFM from the frequency divider FD and the horizontal hold signal HDP; a counter CT12 which compares the output of the AND gate AG7 with a preset value SP and which supplies a signal when the two inputs coincide; a monostable multivibrator MM1 which is triggered by the output of the counter CT12 and which generates a pulse having a predetermined width; an AND gate AG8 for receiving a Q output from the monostable multivibrator MM1 and the horizontal hold signal HDP; a monostable multivibrator MM2 which is triggered by the output of the AND gate AG8 and which supplies a pulse having a predetermined width; a monostable multivibrator MM3 which is triggered by a $\overline{Q}$ output (falling edge) from the monostable multivibrator MM2 and which supplies a pulse having a predetermined width; and an AND gate AG9 for receving a Q output from the monostable multivibrator MM3 and a clock pulse from the oscillator OSC10. On the display CRT screen, a screen section which does not interfere with the display of data, (for example, the lower section of the screen) is utilized as the section for displaying the area value with timing determined by the display timing signal generator GP. When the horizontal hold lines of the CRT display number 525, the display timing signal generator GP produces gate pulses corresponding to up to several tens of lines of the lower section and superposes a sampling clock pulse for readout on the gate pulses so that a signal SGP clock pulse signal is generated. The output of the conversion table ROM10, which is the normalized data, is transferred to the second memory MEM2 within the memory unit 9, the maximum value position data from the comparator CMP2 is transferred to the third memory MEM3, and the abnormal value data and the data designating the area value pattern for the range of the abnormal values are transferred to the fourth memory MEM4 through an OR gate OG1.

The mode of operation of the component units will be described with reference to FIGS. 12(A) to 12(M), FIGS. 13(A) to 13(F), and FIGS. 14(A) to 14(F), in which timing charts are shown.

Figure 12:
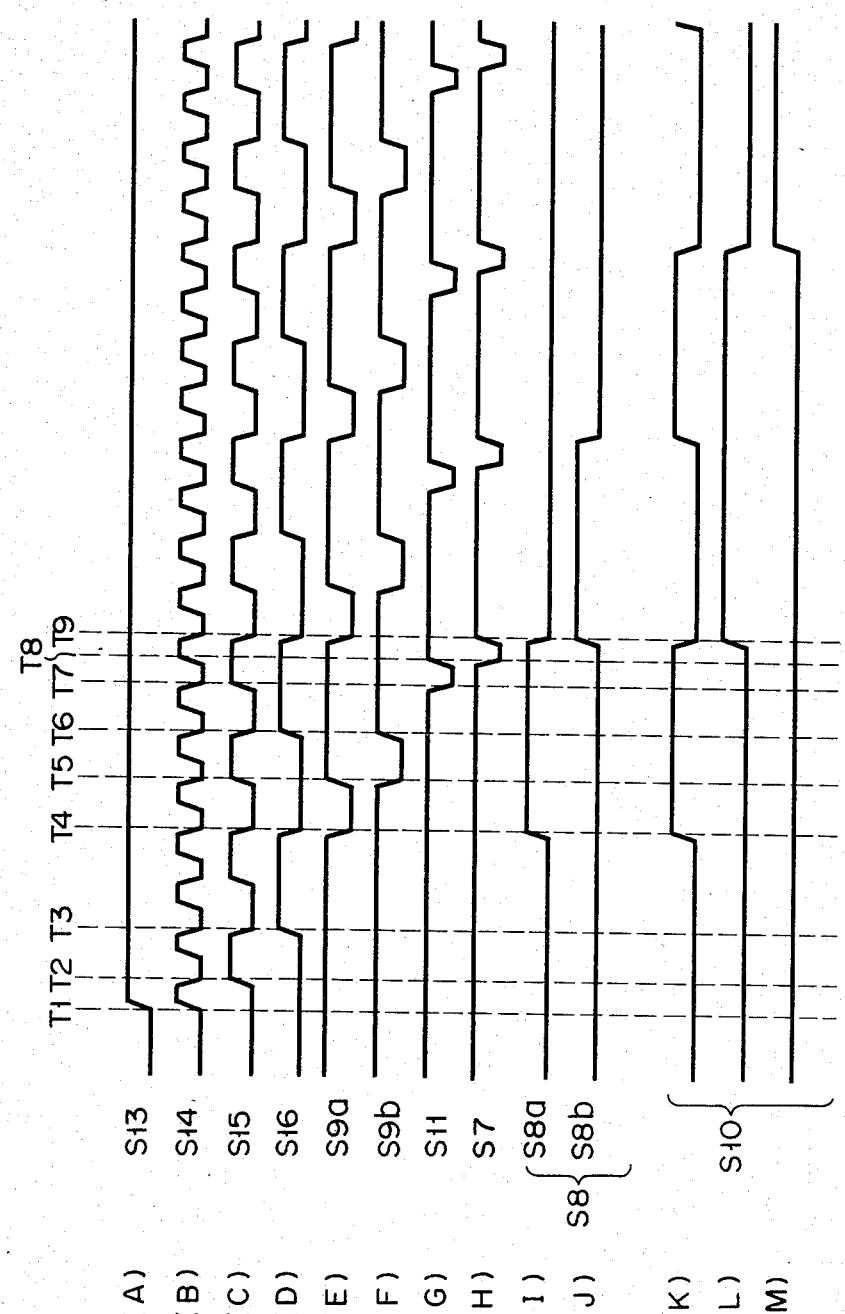
FIGS. 12(A) to 12(M) are timing charts for explaining the operation of the first embodiment shown in FIG. 5.
Figure 13:
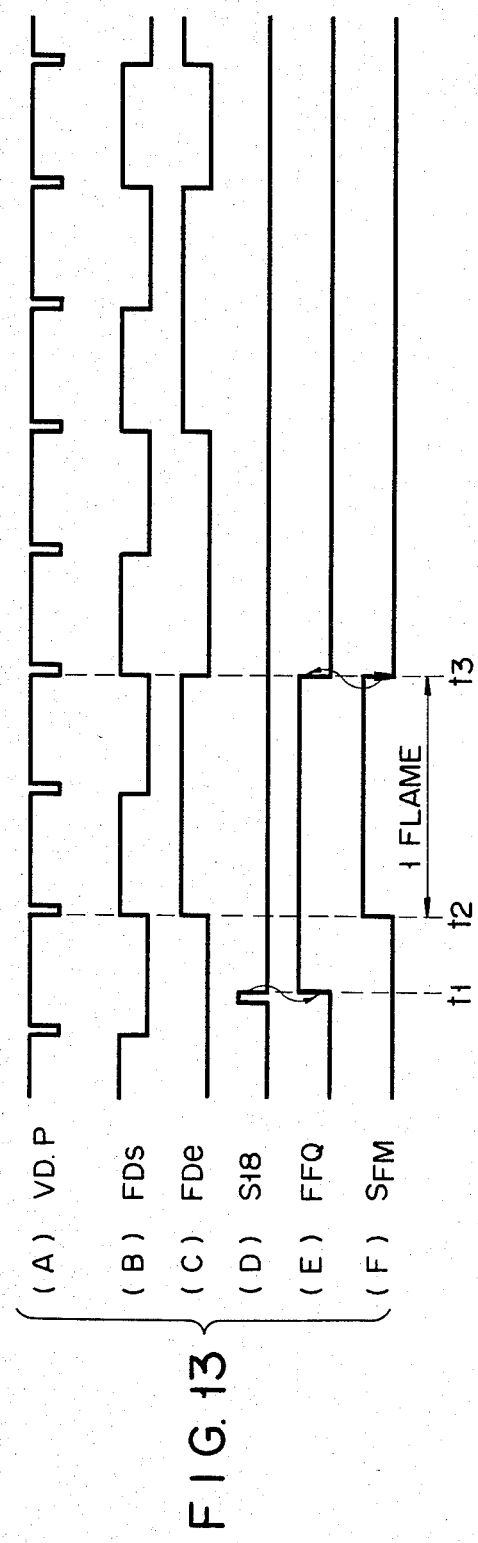
FIGS. 13(A) to 13(F) and FIGS. 14(A) to 14(F) are timing charts for explaining the operation of the data processing unit shown in FIG. 11.
Figure 14:
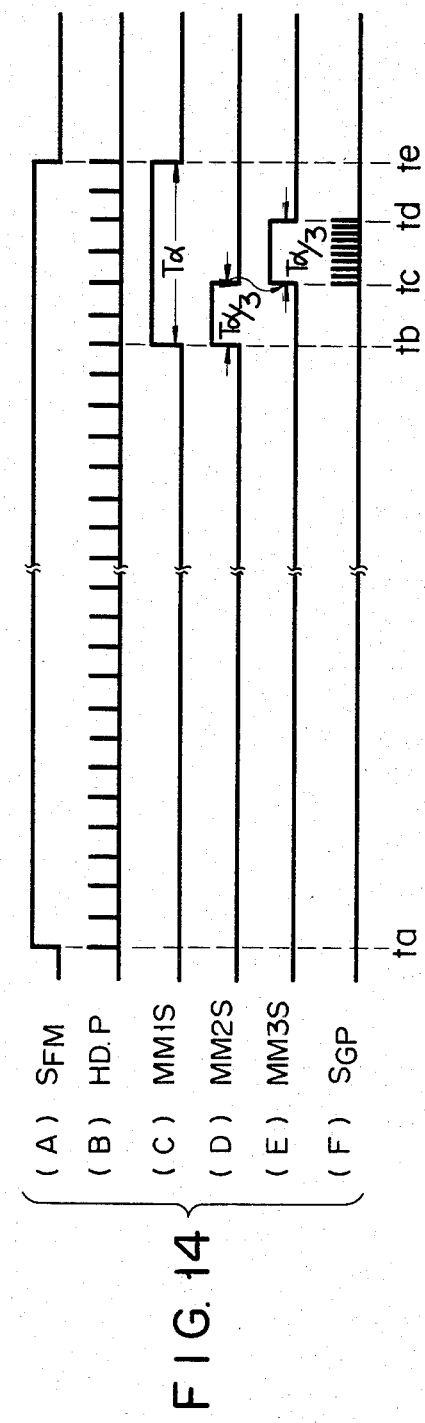

After the power is turned on, the electrodes 2a and 2b are attached at a predetermined position, for example, the upper and lower portion of the breast, as shown in FIG. 5. When the pushbutton switch PB1 for starting is turned on (time T1), the oscillator OSC within the timing control circuit 5 is activated and the pulse signal S14 is output from the output end of the inverter IC8, as shown in FIG. 12(B). The first JK flip-flop IC10 in the timing control circuit 5 is then activated (time T2 of FIG. 12(C)) and the second JK flip-flop IC11 is also activated (time T3 of FIG. 12(D)). Therefore, the NAND gate IC16 is activated and the analog switch gate signal S9a for selecting a low frequency fL is output (time T4 of FIG. 12(E)). The analog switch AS3a for selecting the low frequency fL of the reference voltage generator 6 is turned on and a sinusoidal voltage E of the low frequency fL is applied from the Wien bridge oscillator 6A. Therefore, an output signal S12L from the voltage follower 6B is calculated by the following relation (11):

$$S12L = E\sin(2\pi fL)t \tag{11}$$

Since this signal S12L is input to the capacitance measuring unit 3 and the least significant bit (to be referred to as the LSB) of the parallel output signal S8 of the shift register IC12 within the timing control circuit 5 is activated, the analog switch AS1a is turned on in response to the signal S8a (FIG. 12(I)). An output signal S2L is obtained from the capacitance measuring unit 3, which is given by the following relation (12). (This signal is actually amplified in absolute value by the absolute value circuit 3B).

$$S2L = \left| (-1/R5 \cdot CL) \int_0^t S12d \right| \tag{12}$$

$$= E/(2\pi fL \cdot R5 \cdot CL) \cdot \cos(2\pi fL)t$$

Further, the analog switch AS2a is turned on by the analog switch gate signal S9a, and the signal S2L is input to the peak value detecting and holding circuit 4a. If the peak value amplification is defined to be 1, the output signal S3a is calculated by the following relation (13) and is held constant:

$$S3a = \max(S2L) = E/(2\pi \cdot fL \cdot R5 \cdot CL) \tag{13}$$

The analog switch gate signal S9b for selecting a high frequency fH from the lower NAND gate IC17 within the timing control circuit 5 is activated (time T5 of FIG. 12(F)), the analog switch AS3b of the reference voltage generator 6 is turned on and an output signal, S12H, the value of which is shown by the following relation (14), is supplied:

$$S12H = E\sin(2\pi fH)t \qquad (14)$$

Therefore, an output signal S2H is output from the capacitance measuring unit 3, as its value is shown by the following relation (15):

$$S2H = E/(2\pi fH \cdot R5 \cdot CH)|\cos(2\pi fH)t| \qquad (15)$$

Further, this signal S2H is supplied to the peak value detecting and holding circuit 4b through the analog switch AS2b, and an output signal S3b thereof is given by the following relation (16):

$$S3b = E/(2\pi fH \cdot R5 \cdot CH) \qquad (16)$$

Thus, the obtained output signals S3a and S3b are input to the division unit 7. The ratio of the signal S3a to the signal S3b is calculated at the division unit 7 and a signal S4, the value of which is given by the following relation (17), is output from the division unit 7:

$$S4 = S3a/S3b = (fL/fH) \cdot (CL/CH) \qquad (17)$$

Since the value (fL/fH) is a known constant, the ratio of the capacitances is given by the signal S4 taken with relations (6) and (9). The output signal S4 is converted to a digital signal S5 at the ADC 8 and this digital signal S5 is stored in the memory unit 9. This storage is performed by activating the counter IC13 and the NAND gate IC15 in the timing control circuit 5 (time T7 of FIG. 12(G)). That is, the parallel output address selection signal S10 is obtained when the counter IC13 is activated (FIGS. 12(K) to 12(M)), the memory latch signal S11 is obtained when the NAND gate IC15 is activated (FIG. 12(G)), and a combination thereof causes the digital signal S5 to be stored in a predetermined address. In this case, the memory unit 9 is arranged so as to constitute an area corresponding to the electrode 2a of an array or matrix form. When the signal S5 is stored, the signal is stored in the corresponding address in synchronism with the analog switch gate signal S8 for switching each cell of the electrode 2a.

Therefore, the uppermost NAND gate IC14 in the timing control circuit 5 is activated to supply the reset signal S7 (T8 of FIG. 12(H)). The capacitance measuring unit 3 and the peak value detecting and holding circuits 4a and 4b are reset by this reset signal S7.

In a similar manner as above, the operation is repeated for all the electrode cells. The digital signal S5, based on the value of the signal S4 obtained by relation (17) and corresponding to each electrode cell, is stored at a predetermined address in the first memory MEM1 within the memory unit 9. An output signal S17 of the display counter CT10 within the display control section 10A as the address selection signal obtained through the data selector SEL specifies the readout address, and the memory data (data signal S6) in the first memory MEM1 is sequentially transferred to the data processing unit 11. In the data processing unit 11, the minimum and maximum value determining circuits determine the minimum and maximum values of the data signal S6 within the first memory MEM1. The minimum value is stored in the buffer BUFL and the maximum value is stored in the buffer BUFM. On the other hand, the data signal S6 is directly supplied to the conversion table ROM10 and is converted to a normalized value data at the conversion table ROM10. The normalized value data is sequentially stored in the second memory MEM2 according to the address selection signal S17. When the maximum value from the buffer BUFM and the sequentially supplied data signal S6 which are input to the comparator CMP2 coincide, that is, when the data signal S6 transfers the maximum data, the comparator CMP2 outputs a coincidence signal and the data indicating the position thereof is stored in a predetermined address of the third memory MEM3. Further, the minimum and maximum values output from the buffer BUFL and BUFM, respectively, are supplied to the threshold decision circuit THDG. The threshold decision circuit THDG, for example, generates a threshold value signal which designates an arithmetic mean of the minimum and maximum values. The comparator CMP3 compares the threshold value signal and the data signal S6 to judge the presence or absence of abnormal cells. The resultant binary data are sequentially stored in the fourth memory MEM4.

A case in which data designating the area of the abnormal cell region within the data processing unit 11 is produced will be described with reference to the timing charts in FIGS. 13(A) to 13(F) and FIGS. 14(A) to 14(F). The frequency divider FD, for example, has two flip-flops. When the vertical hold signal VDP is input to the flip-flop of the first stage (FIG. 13(A)), a pulse signal FDs for one period is produced (FIG. 13(B)) and a pulse signal FDe corresponding to the duration from a leading edge of the pulse signal FDs to the next leading edge is output from the flip-flop of the second stage. That is, the pulse signal FDe becomes the timing signal SFM which corresponds to two (one frame) of the vertical hold signals VDP. Therefore, when the panel control signal S18 is input, the flip-flop FF is set by the trailing edge (FIG. 13(D)) immediately after the panel control signal S18 is produced. The AND gate AG6 is then opened by output FFQ (FIG. 13(E)) of the flip-flop FF and is activated by the vertical hold signal VDP input immediately thereafter. A frequency dividing signal corresponding to one frame from the time in which the flip-flop FF is activated (t2 of FIG. 13(F)) is produced. When the time for one frame elapses, the output signal SFM of the frequency divider FD falls and the flip-flop FF is reset at this timing (time t3 of FIG. 13(F)) and the AND gates AG5 and AG6 are closed. Since the abnormal value data of the comparator CMP3 which corresponds to the duration of one frame is input to the counter CT11 through the AND gate AG5, counting of the number of data within the region of the abnormal cells is performed, and the count value is input to the character generator ROM20. The input value data is converted to the value pattern data. The display timing of the value pattern data is controlled by the operation of the display timing signal generator GP. This mode of operation will be described with reference to FIGS. 14(A) to 14(F). In this embodiment, there are 525 lines of the horizontal hold signal HDP within the period of the signal SFM corresponding to one frame. Up to several tens of lines at the lower section are used for displaying the value pattern, according to which the counter CT12 of the display timing signal generator GP is preset to the value "N". The horizontal hold signal HDP is applied to the clock end of the counter CT12 through the AND gate AG7. When the pulse number of the signal HDP coincides with the preset value "N", the coincidence signal is generated from the counter CT12 (time ta). As a result, the first monostable multivibrator MM1 is triggered and outputs a pulse signal having a predetermined width Tα (in this case, the width includes the remaining lines of 525 - N of the horizontal hold signal HDP) (FIG. 14(C)). At the same time, the second monostable multivibrator MM2 is triggered and outputs a pulse signal having a predetermined width (one third of the pulse width Tα) (FIG. 14(D)). Then, the third monostable multivibrator MM3 is triggered when the pulse from the second monostable multivibrator MM2 falls, and outputs a pulse having a predetermined width (one third of the pulse width Tα) (FIG. 14(E)). While the pulse produced from the third monostable multivibrator MM3 is generated, clock pulses (obtained by dividing the horizontal hold signal into a plurality of sampling pulses) are applied as the signal SGP (FIG. 14(F)) to the clock terminal of the character generator ROM20 through the AND gate AG9. Therefore, in the character generator ROM20, the pattern of the selected area corresponding to the count value is read out for each bit at the timing of the clock pulse SGP. As a result, within the fourth memory MEM4 of the memory unit 9, for example, data designating the region of the abnormal cells is stored in the area from the first line to the (525 - N)th line corresponding to the CRT display raster. In the remaining lines N, the value pattern data (for example, a two-digit number) indicating the number of abnormal cells is stored. Further, the value pattern data is stored in the middle third of the CRT display screen. When the panel control signal S18 is input again, the counter CT11 is cleared and operates for another detection.

The mode of operation of the display 10 will be described. The respective AND gates AGa to AGc are controlled by the panel control signal S18. The output signals from the AND gates AGa to AGc then turn on the respective switches SW1, SW2, SW4. Switch SW3 is directly controlled by the pannel control signal S18. Data stored in the respective memories MEM1 to MEM4 are then output in response to the selection timing of the display address signal S17. The readout data are transferred to the density conversion table ROM3 and the color conversion tables ROMa to ROMd. Therefore, the data read out from the respective memories MEM1 to MEM4 are first converted to predetermined gradation signals which are suitable for display at the monochrome CRT display CRT1 and are supplied to the monochrome CRT display CRT1 and displayed in black and white through the D/A converter DAC1 and the video amplifier AMP1. At this time, the maximum value portion and the region of the abnormal cells are displayed in the stressed form to distinguish from the other portions. The data read out from the memories MEM1 to MEM4 are respectively supplied to the color conversion tables ROMa to ROMd and are converted to color signals therein. The converted signals are supplied to the color CRT display CRT2 through the D/A converters DACa to DACd and the video amplifiers AMPa to AMPc, and are thus displayed in color. When a specific color, for example, a "red" color signal, alone is selected by the memory contents of the color conversion table ROM2 which receives the output data from the fourth memory MEM4 storing the area value data of the region of the abnormal cells and the abnormal value, the portion in which the abnormal cells are present is displayed in red on the color CRT display CRT2. Further, at a predetermined position, a number indicating the area of the abnormal cells is displayed in red. In this case, during the time in which the address for the portion where the abnormal cells are present is selected, the outputs from the first and second memories MEM1 and MEM2 are suppressed since the AND gates AGa and AGb are closed. Therefore, in the same address section, other colors may not be mixed in and displayed. When the specific color "yellow" is specified for the memory contents of the density conversion table ROM1 which receives the output data from the third memory MEM3 storing the data designating the position of the maximum value, this portion is displayed in yellow. At this time, the respective gates AGa to AGc are closed, and other portions will not be displayed in yellow. The position of the maximum value is displayed only in yellow, while the region of the abnormal cells is displayed only in red, thus preventing the mixing of colors. In this way, the desired density and color display are obtained. Further, the abnormal portions are emphatically displayed, so that the abnormal cells are easily detected. As an alternative way of displaying the position of the maximum value, a blinking display, for example, may be employed to emphasize the position of the maximum value. In this way, the portion of the breast which is interposed between the pair of electrodes 2a and 2b is displayed with good contrast and color. The point on the screen which corresponds to cancer cells is emphasized as a darker point or with a distinguishable color. Therefore, the cancer cells are easily detected. A function may be included in which graphic display such as a histogram or detailed numerical display is adopted together with the density display in the display unit 10, and each image is simultaneously displayed, so that a further improvement in precision of measurement is achieved.

When the range of the skin of the body exceeds the area of the electrode 2a, the electrodes 2a and 2b must be relocated to other positions. When a series of operations for measurement is completed, the pushbutton switch PB2 disposed on the timing control circuit 5 is turned off to halt all functions of the device. When the entire measurement is completed, the pushbutton switch PB2 is also turned off. With a measuring device of this type in the embodiment according to the present invention, the abnormal cells are properly detected even if the distance between the electrodes is not constant. Further, since the distance between the electrodes is short, the amount of current flowing through the body is extremely small, thus assuring safety. The device according to the present invention has a simple structure, so that the design results in compactness and low manufacturing cost.

Figure 15:
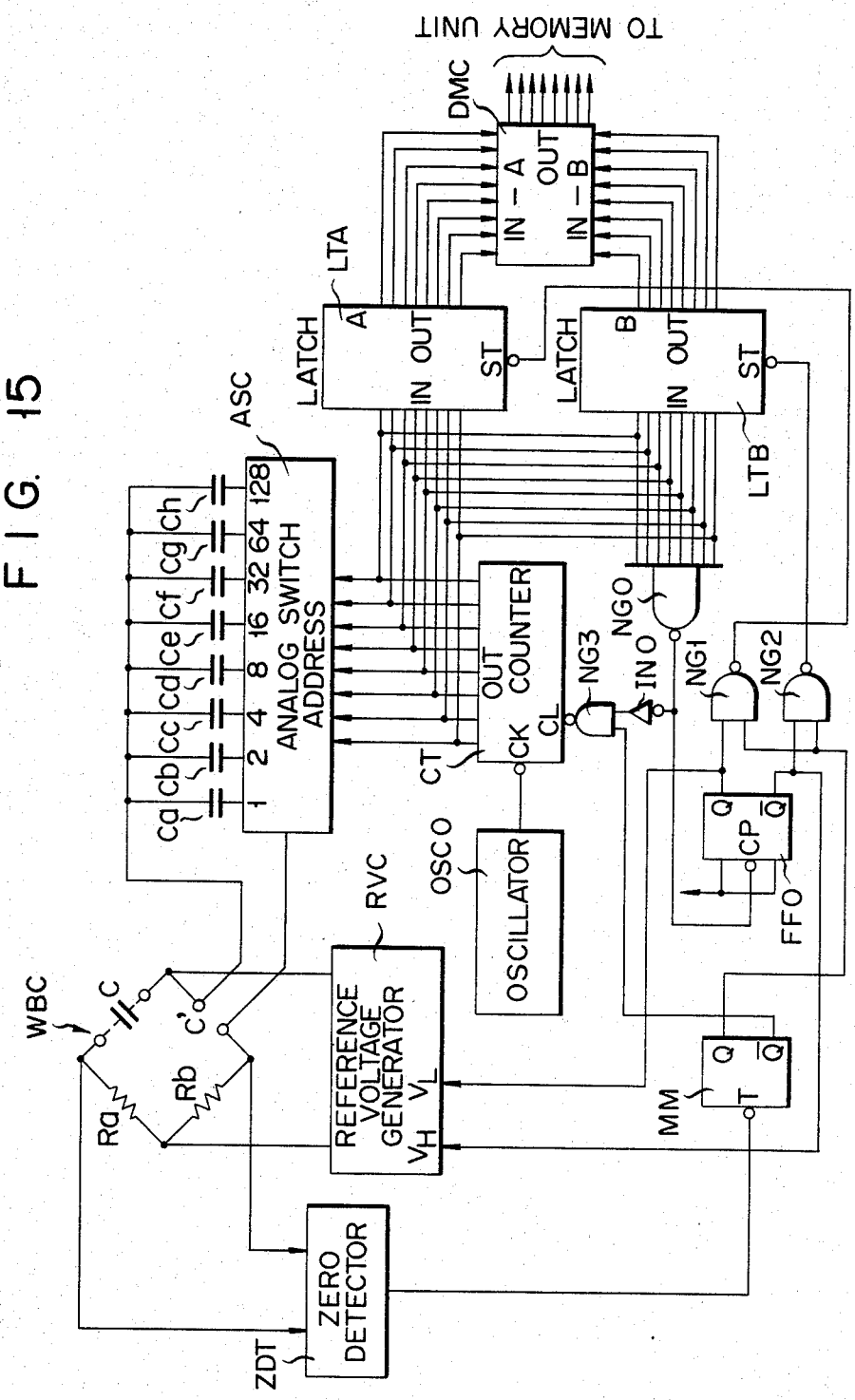
FIG. 15 is a schematic block diagram illustrating an arrangement of a second embodiment of the abnormal cell detecting device according to the present invention.

FIG. 15 is a schematic circuit diagram illustrating a partial arrangement of a second embodiment according to the present invention. This circuit has a Wheatstone bridge circuit WBC (to be referred to as the bridge circuit hereinafter) having resistors Ra and Rb and capacitors C and C'. The capacitor C (equivalent to electrostatic capacitance of the organ), which is obtained by sequentially driving the electrode cells of the electrodes 2a and 2b, is connected to a pair of terminals, while the variable capacitor C', which is selected by an analog switch circuit ASC to be described later, is connected to another pair of terminals. A reference voltage generator RVC which has the same function as the reference voltage generator in the first embodiment and which generates a reference voltage VL for the low frequency fL and a reference voltage VH for the high frequency fH based on a selection signal is connected to the power source terminals of the bridge circuit WBC. A zero detector ZDT is connected to the output terminals of the bridge circuit WBC. Therefore, when the impedances of the elements are as follows, $Ra=\dot{Z}1$, $Rb=\dot{Z}2$, $C=\dot{Z}3$, and $C'=\dot{Z}4$, $\dot{Z}1=\dot{Z}2$ and $\dot{Z}1 \cdot \dot{Z}3=\dot{Z}2 \cdot \dot{Z}4$, the zero detector ZDT operates and the desired output is obtained. That is, when the capacitance of the capacitor C equals the capacitance of the variable capacitor C' ($\dot{Z}3=\dot{Z}4$), the desired output is obtained.

The analog switch circuit ASC is of address type in which a plurality (8 in the figure) of capacitors are connected in parallel. A plurality of analog switches and a decoder for selectively controlling the analog switches are further included therein. A counter CT performs a counting operation by the output of an oscillator OSC0, and the outputs are sequentially supplied from a plurality of output terminals (8 bits in the figure). In accordance with the counter output, an address of the analog switch circuit is selected and the decoder generates a combined signal (255) of 8 bits so that the corresponding analog switch is turned on to determine the capacitance of the variable capacitor C'. Therefore, if capacitances of respective capacitors Ca to Ch are 1, 2, 4, 8, 16, 32, 64, and 128 pF, a desired capacitance may be selected in the range of 1 to 255 pF by a combination of capacitances of the capacitors Ca to Ch. The output signal of 8 bits from the counter CT is applied to the input terminals of latches LTA and LTB and then to the input terminal of a NAND gate NG0. The NAND gate NG0 produces an output of level "0" every time the counter CT counts the maximum counting value (255) and the outputs of all the bits coincide. A flip-flop FF0 for switching the reference voltages is turned on by the output of "0" level. The flip-flop FF0 is a clock type flip-flop in which the Q output is inverted to the $\overline{Q}$ output and vice versa every time the NAND gate NG0 produces the output of "0" level. In accordance with the respective Q and $\overline{Q}$ outputs, reference voltage VH at high frequency fH from the reference voltage generator RVC is switched to the reference voltage VL at low frequency fL or vice versa.

On the other hand, a monostable multivibrator MM is connected to the output end of the zero detector ZDT. The monostable multivibrator MM is triggered by the output of the zero detector ZDT and supplies an inverted output for a predetermined period of time. The Q or $\overline{Q}$ output of the monostable multivibrator MM is input to one end each of respective NAND gates NG1 and NG2, respectively. The Q or $\overline{Q}$ output of the clock type flip-flop FF0 is supplied to the other end each of the respective NAND gates NG1 and NG2, respectively. The output from the NAND gate NG1 is supplied to a strobe terminal of the latch LTA, and the other output from the NAND gate NG2 is supplied to a strobe terminal of the latch LTB. The output of a NAND gate NG3 which receives the inverted signal (inverted by an inverter IN0) of the NAND gate NG0 and the $\overline{Q}$ output of the monostable multivibrator MM is input to the clear terminal of the counter CT. The counter CT is normally cleared when completing the counting operation. At this time, if the zero detector ZDT supplies an output and the monostable multivibrator MM is triggered, the clearing operation is temporarily stopped, thus preventing trouble in measurement and detection. The outputs from the latches LTA and LTB are respectively supplied to input terminals IN-A and IN-B of a digital dividing circuit DMC. The output data from the digital dividing circuit DMC is stored in the memory unit as described in the first embodiment.

The mode of operation of the circuit shown in FIG. 15 will be described with reference to FIGS. 16(A) to 16(H) showing timing charts. In this circuit, analog switches as used in the first embodiment are used for switching the respective electrode cells. In this case, when the counter performs two counting operations (that is, when the reference voltage generator RVC generates the first reference voltage VH once and the second reference voltage VL once), and when this operation is defined as one cycle, the electrode cells are switched with the timing of the trailing edge of the $\overline{Q}$ output of the flip-flop FF0; thus the electrode cells are switched in synchronizm with the switching timing of each cycle.

Figure 16:
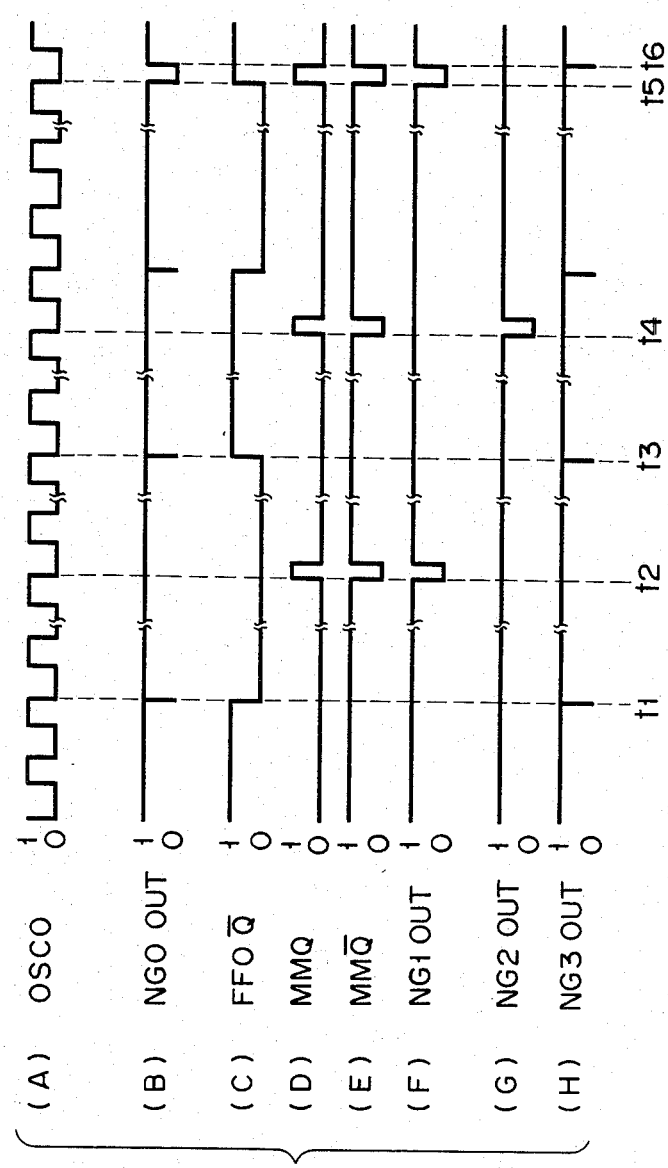
FIGS. 16(A) to 16(H) are timing charts for explaining the operation of the second embodiment shown in FIG. 15.

When the counter CT counts the maximum value (255) at time t1 as shown in FIG. 16(A) and outputs of the respective bits coincide, the outputs of the NAND gates NG0 and NG3 sequentially reach level "0" (time t1 of FIGS. 16(B) and 16(H)). At the same time, the counter CT is cleared and the flip-flop FF0 produces the Q output of level "1" (time t1 of FIG. 16(C)). The reference voltage VL is generated from the reference voltage generator RVC and this voltage is supplied to the bridge circuit WBC. The NAND gate NG0 immediately produces the output signal of "1", triggering the NAND gate NG3 to produce the same output signal of "1". Therefore, the counter CT initiates the counting operation. With the timing synchronized with the counting operation, the first electrode cell is selected so that the capacitor C (capacitance of the organ) is connected to one pair of the capacitor terminals of the bridge circuit WBC. In response to the operation of the counter CT, addresses of the analog switch circuit ASC are sequentially selected to switch the analog switches, and the capacitance of the variable capacitor C' gradually increases. When the capacitances (impedances) of the capacitors C and C' coincide, the zero detector ZDT produces an output to trigger the monostable multivibrator MM. The Q output of the monostable multivibrator MM becomes level "1" (time t2 of FIGS. 16(D) and 16(E)). The gate of the NAND gate NG1 which receives the Q output from the flip-flop FF0 is opened (t2 of FIG. 16(F)). A strobe signal is supplied to the first latch LTA and the current count value of the counter CT is latched. The digital value of the counter CT corresponds to the capacitance of the capacitor C of the body when the reference voltage VL is applied.

The counting operation of the counter CT is completed once, so that the outputs of all the bits become the same. The output of the NAND gate NG0 becomes level "0" again (time t3 of FIG. 16(B)) and the output of the NAND gate NG3 becomes level "0" accordingly (t3 of FIG. 16(H)). Therefore, the counter CT is cleared. At the same time, the output from the flip-flop FF0 is inverted and the $\overline{Q}$ output becomes level "1" (time t3 of FIG. 16(C)), so that the reference voltage of the reference voltage generator RVC is switched to the reference voltage VH and this voltage is applied to the bridge circuit WBC. Thereafter, in the same manner described above, the capacitance of the capacitor C of the organ and that of the variable capacitor C' are compared and if they coincide, the zero detector ZDT outputs a signal. Thus, the monostable multivibrator MM is triggered again to produce the Q output of level "1" (time t4 of FIGS. 16(D) and 16(E)). The gate of the NAND gate NG2 which receives the $\overline{Q}$ output from the flip-flop FF0 is opened (time t4 in FIG. 16(G)), and the strobe signal is supplied to the second latch LTB. As a result, the current count value of the counter CT is latched in the latch LTB. In this way, the latched digital value corresponds to the capacitance of the organ when the reference voltage VH is applied.

As described above, when two digital data which correspond to the capacitances when the reference voltages VL and VH, respectively, are supplied with this latched timing, the digital dividing circuit DMC operates and outputs a signal corresponding to the ratio of the digital data. The output data is stored in the predetermined address in a similar memory unit to the one shown in the first embodiment.

The operation described above is repeated every time the respective electrodes cells are switched. All the data are then stored in the memory unit and the operation for display is performed to measure and detect the abnormal cells.

When an output is produced from the zero detector ZDT before the counting operation of the counter CT is completed, erratic operation with respect to the clearing operation of the counter CT may occur. However, in the circuit according to the second embodiment, the combination of the inverter IN0 and the NAND gate NG3 completely prevents erratic operation. When the capacitance of the capacitor C of the organ coincides with the maximum capacitance (selected at 255th bit) of the variable capacitor C' at time t5 immediately before the coincidence signal of all bits of the counter CT as shown in FIG. 15 is produced, the $\overline{Q}$ output from the monostable multivibrator MM becomes level "0" (times t5 to t6 of FIG. 16(E)) so that the NAND gate NG3 does not open for the duration (times t5 to t6 of FIG. 16(H)). When the $\overline{Q}$ output becomes level "1", the counter CT is cleared (time t6 of FIG. 16(H)). Therefore, the digital data which is latched at the latch LTA may not be different from the actual data.

In the device of this type according to the embodiment of the present invention, in addition to the advantages described in the first embodiment, the signal processing circuits operate with digital values so that the device becomes compact and light in weight and is manufactured at low cost. Further, the reliability of the operation of the circuits is greatly increased with excellent operability.

Figure 17:
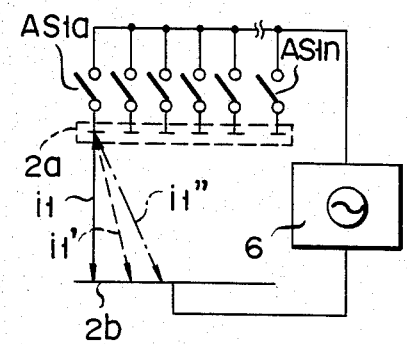
FIGS. 17 and 18 are schematic views illustrating arrangements of electrodes used for the first and second embodiments.
Figure 18:
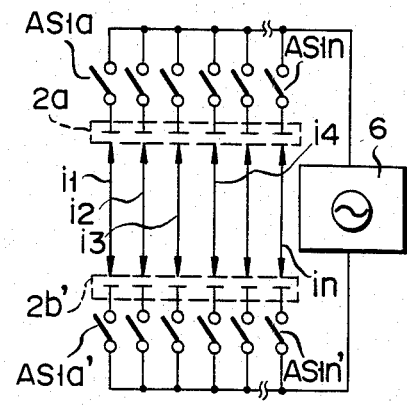

Further, in the first and second embodiments, the pair of electrodes 2a and 2b is an assembly having n divided cells, while the electrode 2b is constituted by a single plate electrode as shown in FIG. 17. In this case, the current path between the electrodes 2a and 2b which is selected by the analog switch AS1a is not necessarily the shortest path i1 between the electrodes 2a and 2b. The current path is selected in order to minimize the impedance of the path. The path may be path i1' or i1", which are longer than the shortest path i1. Therefore, a correspondence between the matrix-shaped divided cells of the electrode 2a and the current paths may hardly be achieved. As shown in FIG. 18, the electrode 2b may be constituted by n electrode cells in the same manner as in the electrode 2a. Further, analog switches AS1a' to AS1n', the arrrangement of which is the same as that of the analog switches AS1a to AS1n, and which are controlled and driven in the same manner as the analog switches AS1a to AS1n, are formed in correspondence with the analog switches AS1a to AS1n. The current paths between the analog switches are shown by i1, i2, i3, . . . in FIG. 18, so that the electrode cells of the electrode 2a respectively correspond to those of the electrode 2b. Thus, the correspondence between current paths and the cells is established, increasing the detecting precision on the display screen.

Figure 19:
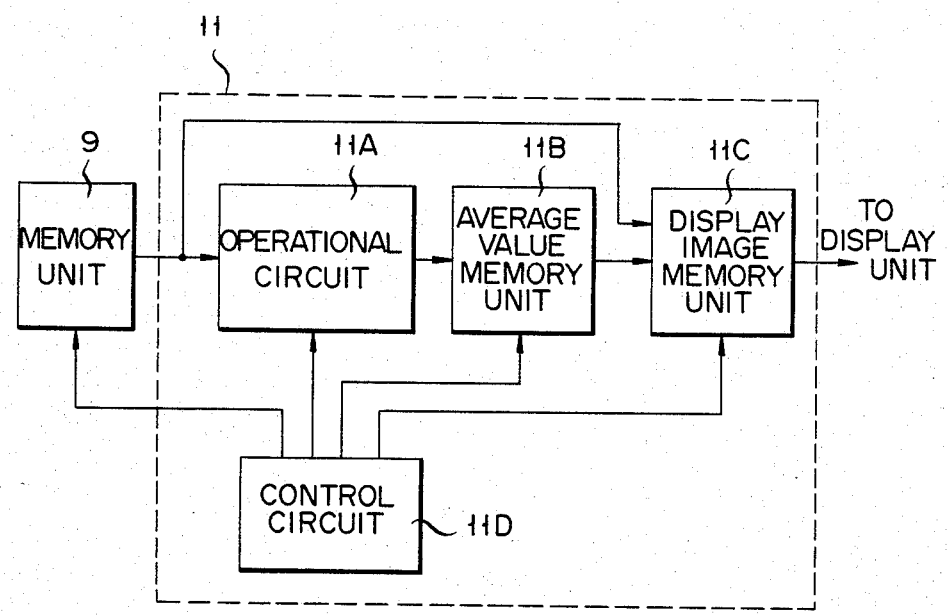
FIG. 19 is a schematic block diagram illustrating another arrangement of the data processing unit shown in FIG. 5.

The data processing unit 11, for example, as shown in FIG. 19, may comprise an operational circuit 11A (for example, a digital arithmetic circuit) for calculating the average value of the memory data in the memory unit 9 by combining several data and for outputting the calculate value; an average value memory unit 11B for temporarily storing the output from the operational circuit 11A in a corresponding address; a display image memory unit 11C for synthesizing the memory data from the average value memory unit 11B and the memory data of the memory unit 9 and for storing the synthesized data to be displayed; and a control circuit 11D for controlling the operation of each unit.

The mode of operation of the data processing unit 11 will be described with reference to FIG. 20, FIGS. 21(A) to 21(E), and FIG. 22. Data P11-P1n, P11-Pn1, . . . detected by the electrode 2a having divided cells which are disposed in a matrix form of rows (S11-S1n)×(S11-Sn1) as shown in FIG. 20 are stored in a matrix form, corresponding to the divided cells (S11-S1n)×(S11-Sn1). Data P11-Pnn detected at the respective divided cells S11-Snn are regarded as data obtained at central portions of the individual cells. Based on this data of the memory unit 9, an operation as shown in FIGS. 21(A) to 21(E) is performed according to an operation program by a command from the control circuit 11D, and the results are sequentially stored in the average value memory unit 11B.

Average values (P11+P12)/2 and (P12+P13)/2 of data (P11, P12) and (P12, P13) are calculated by using sets (S11, S12) and (S12, S13) of two adjacent cells in the row direction. The calculated results, as shown in FIGS. 21A and 21B, may be regarded as the central data of imaginary divided cells S100 and S101 formed and surrounded by the central lines of the divided cells S11, S12 and S13. The calculated data are stored in a matrix form, corresponding to the matrix of the divided cells, in the average value memory unit 11B. Each data is sequentially shifted in the row direction and the average value of the two adjacent data is calculated. The calculated average value is stored in the corresponding position of the matrix. The operation is repeated for the remaining rows.

Average values (P11+P21)/2 and (P21+P31)/2 of data (P11, P21) and (P21+P31) are subsequently calculated by using sets (S11, S21) and (S21, S31) of two adjacent cells in the column direction. The calculated results, as shown in FIGS. 21C and 21D, may be regarded as the central data of imaginary divided cells S110 and S111 formed and surrounded by the central lines of the divided cells S11, S21, S31. The calculated data are stored in a matrix form, corresponding to the matrix of the divided cells, in the average value memory unit 11B. Each data is sequentially shifted in the column direction and the average value of the adjacent data is calculated. The calculated average value is stored in the corresponding position of the matrix. The operation is repeated for the remaining columns.

Finally, an average value (P11+P12+P21+P22)/4 of data (P11, P12, P21, P22) are calculated by using a set (S11, S12, S21, S22) of four adjacent divided cells. The calculated result, as shown in FIG. 21E, may be regarded as the central data of an imaginery divided cell S200 having four vertices which are defined by the central points of the divided cells S11, S12, S21 and S22. The calculated data is stored in the average value memory unit 11B in a matrix form. The set of data is formed by shifting the cells to be selected in the row and column directions. The average values are calculated in the same manner as described above, and the results are stored in the positions corresponding to the matrix.

In this manner, the average value memory unit 11B, as shown in FIG. 20, stores the average value data corresponding to the matrix of the divided cells at the central section of the common line segments between the respective divided cells. The data of the average value memory unit 11B and the data of the memory unit 9 are sequentaily read out by the control circuit 11D and the readout data are written in the corresponding addresses in the display image memory unit 11C. As a result, the arrangement of the data in the display image memory unit 11C is such that, as shown by a number of block points in FIG. 22, the display image data at the central sections of the matrix S11–Snn of the divided cells is stored in a matrix form. Further, the display image data at the central sections of the common line segments of the divided cells are also aligned in a matrix form, in correspondence with the display image data described above.

When an image is displayed on the display unit 10, based on this kind of memory data stored in the display image memory unit 11C, the densities of the dark and light colors are finely controlled and the detection precision is also improved. The operational process in the data processing unit 11 may be controlled by various techniques with a microcomputer.

The present invention is not limited to the embodiments described herein, but may be extended to various changes and modifications within the spirit and scope of the present invention.

What is claimed is:

1. A method for detecting an abnormal cell, comprising the steps of:
    attaching at least a pair of electrodes to a portion of a body to be measured, at least one electrode of said pair being formed of a plurality of electrode cells;
    supplying each of said electrode cells with first and second voltages having different frequencies between said electrodes;
    independently detecting from between each electrode cell of one electrode and the other electrode of said electrode pair, first and second impedance values, said values being obtained from the body portion being measured when the first and second voltages are supplied across said electrodes;
    calculating a plurality of ratios by dividing the first and second impedance values obtained from each cell;
    storing in a memory, at predetermined addresses corresponding to the locations of each of said electrode cells, the ratios calculated for each of said electrode cells during said calculating step;
    determining the existence of an abnormal data representing said abnormal cell based upon said calculated ratios;
    selecting the address of said memory at which said abnormal data is stored, so that said abnormal data is read out in accordance with the selected address;
    producing an image data corresponding to said abnormal cell based on the read-out abnormal data; and
    displaying the produced image data in the form of various visual images,
    said frequencies of the first and second voltages being selected so as to border the range of dispersion of frequency-specific inductive capacity of the cells of said body portion, whereby a difference between the electrostatic capacitances measured at the body portion at the two frequencies is made great.

2. A method for detecting an abnormal cell, comprising the steps of:
    attaching at least a pair of electrodes to a portion of a body to be measured, at least one electrode of this pair being formed of electrode cells;
    supplying each of said electrode cells with first and second voltages having different frequencies between said electrodes;
    independently detecting from between each electrode cell of one electrode and the other electrode of said electrode pair, first and second impedance values obtained from the body portion being measured when the first and second voltages are supplied across said electrodes;
    calculating a plurality of ratios by dividing the first and second impedance values obtained from each cell by said detecting step; and
    deciding the presence or absence of abnormal cells in the body portion based on the calculated plurality of ratios,
    said frequencies of the first and second voltages being selected so as to border the range of dispersion of frequency-specific inductive cacacity of the cells of said body portion, whereby a difference between the electrostatic capacitances measured at the body portion at the two frequencies is made great.

3. A method for detecting abnormal cells at a body portion to be examined, comprising the steps of:
    attaching first and second electrodes to a portion of a body to be examined, at least said first electrode being formed of a plurality of electrode cells;
    supplying between each of said electrode cells of said first electrode and said second electrode, first and second voltage signals having different frequencies, said different frequencies being selected so as to border the range of dispersion of frequency-specific inductive cacacity of the cells of said body portion, whereby the difference between the electrostatic capacitances measured at the body portion at the two frequencies is great;
    independently detecting, from between each electrode cell of one electrode and the other electrode of said electrode pair, first and second impedance values obtained from the body portion being examined when the first and second voltage signals are supplied across said electrodes;
    calculating a plurality of ratios by dividing the first and second impedance values obtained from each electrode cell during said detecting step;
    storing in a memory section of a memory means at a predetermined address the ratio calculated for each of said electrode during said calculating step;
    processing data by selecting the address of said memory means at which an abnormal data representing an abnormal cell is stored, so that an image data corresponding to said given data is outputted; and
    displaying said image data in the form of various visual images,
    said data processing steps including the steps of storing in a first memory section of said memory means the results of said calculating step, computing and storing in a second memory section of said memory means a normalized value based on the contents of said first memory section, computing and storing in a third memory section of said memory means data designating the location of the maximum values of the contents of said first memory section, and computing and storing in a fourth memory section of said memory means abnormal value data designating the position of any abnormal cells in said body portion being examined based on the contents of said first memory section.

4. A method according to claim 3, wherein said displaying step includes the steps of converting the output data from said first to fourth memory sections to a color data and displaying said color data on a color CRT display.

5. A method according to claim 4, wherein said displaying step further includes the step of supplying the output data from said first to fourth memory sections to a monochrome CRT display.

6. A method according to claim 3, wherein said data processing step includes calculating an average value of a plurality of data stored in said first memory section; temporarily storing said average value; comparing said temporarily stored average value with the data from said first memory section; and synthesizing said image data based upon the results of said comparing step.

* * * * *